(12) United States Patent
Wiesner et al.

(10) Patent No.: US 7,371,854 B2
(45) Date of Patent: May 13, 2008

(54) METHOD FOR THE PRODUCTION OF BICYCLIC AROMATIC AMINO ACIDS AND INTERMEDIATE PRODUCTS THEREOF

(75) Inventors: Matthias Wiesner, Seeheim-Jugenheim (DE); Bernd Neff, Stockstadt (DE)

(73) Assignee: Merck Patent GmbH, Dramstadt (DE)

( * ) Notice: Subject to any disclaimer, the term of this patent is extended or adjusted under 35 U.S.C. 154(b) by 335 days.

(21) Appl. No.: 10/545,168

(22) PCT Filed: Jan. 14, 2004

(86) PCT No.: PCT/EP2004/000210

§ 371 (c)(1),
(2), (4) Date: Aug. 11, 2005

(87) PCT Pub. No.: WO2004/072054

PCT Pub. Date: Aug. 26, 2004

(65) Prior Publication Data

US 2006/0142568 A1     Jun. 29, 2006

(30) Foreign Application Priority Data

Feb. 12, 2003  (DE) ................................ 103 05 784

(51) Int. Cl.
*C07D 265/28*  (2006.01)
*C07D 265/36*  (2006.01)

(52) U.S. Cl. ..................................................... 544/105
(58) Field of Classification Search ................. 544/105
See application file for complete search history.

(56) References Cited

U.S. PATENT DOCUMENTS

| 5,602,145 A | 2/1997 | Samanen |
| 6,117,910 A | 9/2000 | Callahan |
| 2001/0021709 A1 | 9/2001 | Diefenbach et al. |

*Primary Examiner*—Kahsay T Habte
(74) *Attorney, Agent, or Firm*—Millen, White, Zelano & Branigan, P.C.

(57) ABSTRACT

Process for the preparation of integrin inhibitors of the formula (I), in which $R^1$, $R^2$, $R^3$, $R^4$, $R^5$ and X have the meanings indicated in Claim 1, and intermediate compounds

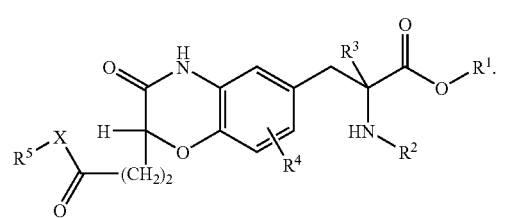

21 Claims, No Drawings

METHOD FOR THE PRODUCTION OF BICYCLIC AROMATIC AMINO ACIDS AND INTERMEDIATE PRODUCTS THEREOF

Bicyclic aromatic amino acids have proven to be suitable templates for the preparation of integrin antagonists.

Compounds from this class of substances are known, for example, from WO 94/29273, WO 96/00730 and WO 96/18602 or known from WO 98/35949

Typical representatives of these substances contain two stereocentres and thus occur in four diastereomeric forms. For a suitable preparation process of such compounds with optimised overall yield, it is particularly important that the reaction be carried out stereoselectively since complex chiral purification can then be avoided.

The invention had the object of finding a novel process for the preparation of compounds, in particular substances which are described in WO 98/35949.

It has been found that reactive derivatives of hydroxyglutaric acid, which facilitate stereoselective construction of the benzoxazinone skeleton by reaction with suitable tyrosine derivatives and result in diastereomerically pure products, can be prepared from enantiomerically pure glutamic acid. In contrast to the synthetic route described in WO 98/35949, the process according to the invention proceeds with virtually no racemisation, and resolution of the diastereomers by chromatography or crystallisation can be avoided.

The invention relates to a process for the preparation of compounds of the formula I

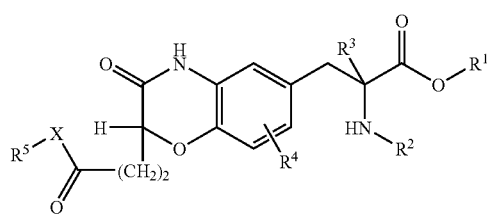

in which
$R^1$ denotes H, alkyl having 1, 2, 3, 4, 5 or 6 C atoms or benzyl,
$R^2$ denotes $R^{10}$, CO—$R^{10}$, COOR$^6$, COOR$^{10}$, CONHR$^{10}$, SO$_2$R$^6$ or SO$_2$R$^{10}$,
$R^3$ denotes H or alkyl having 1-6 C atoms,
$R^4$ denotes H, Hal, OA, NHR$^{10}$, N(R$^{10}$)$_2$, —NH-acyl, —O-acyl, CN, NO$_2$, OR$^{10}$, SR$^{10}$, R$^2$ or CONHR$^{10}$,
$R^5$ denotes NH$_2$, H$_2$N—C(=NH) or H$_2$N—(C=NH)—NH, where the primary amino groups may also be provided with conventional amino-protecting groups, or may be mono-, di- or trisubstituted by $R^{10}$, CO—$R^{10}$, COOR$^{10}$ or SO$_2$R$^{10}$, or $R^6$,
X is absent or denotes NH,
$R^6$ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, NO$_2$, =NH or =O,
$R^9$ denotes H, Hal, OA, NHA, NAA', NHacyl, Oacyl, CN, NO$_2$, SA, SOA, SO$_2$A, SO$_2$Ph or SO$_3$H,
$R^{10}$ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by $R^9$, and in which one, two or three methylene groups may be replaced by N, O and/or S,
Ar denotes mono- or bicyclic aromatic ring system having 0, 1, 2, 3 or 4 N, O and/or S atoms which is unsubstituted or mono-, di- or trisubstituted by A and/or $R^9$,
Ph denotes phenyl which is unsubstituted or mono-, di- or trisubstituted by A,
Hal denotes F, Cl, Br or I and, and pharmaceutically usable derivatives, solvates and stereoisomers thereof, where
a) 5-oxotetrahydrofuran-2-carboxylic acid is reacted with a compound of the formula II

in which
$R^7$ denotes benzyl or alkyl having 1, 2, 3, 4, 5 or 6 C atoms and
L denotes Cl, Br, I or a free or reactively functionally modified OH group, to give a compound of the formula III

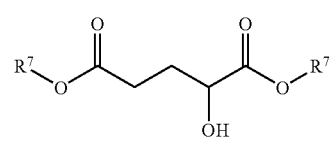

in which
$R^7$ denotes benzyl or alkyl having 1, 2, 3, 4, 5 or 6 C atoms,
b) then a compound of the formula III is reacted with a compound of the formula IV

in which
$R^8$ denotes alkylsulfonyl having 1-6 C atoms or arylsulfonyl having 6-10 C atoms and
L denotes Cl, Br, I or a free or reactively functionally modified OH group, to give a compound of the formula V

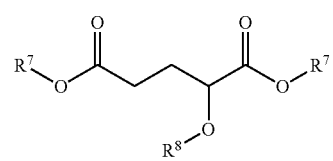

in which
$R^7$ denotes benzyl or alkyl having 1, 2, 3, 4, 5 or 6 C atoms and
$R^8$ denotes alkylsulfonyl having 1-6 C atoms or arylsulfonyl having 6-10 C atoms,
c) then a compound of the formula III or V is reacted with a compound of the formula VI

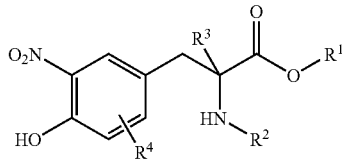

in which
R¹ denotes H, alkyl having 1, 2, 3, 4, 5 or 6 C atoms or benzyl,
R² denotes $R^{10}$, CO—$R^{10}$, COOR⁶, COOR¹⁰, CONHR¹⁰, SO₂R⁶ or SO₂R¹⁰,
R³ denotes H or alkyl having 1-6 C atoms, R⁴ denotes H, Hal, OA, NHR¹⁰, N(R¹⁰)₂, —NH-acyl, —O-acyl, CN, NO₂, OR¹⁰, SR¹⁰, R² or CONHR¹⁰,
R⁶ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, NO₂, =NH or =O,
R⁹ denotes H, Hal, OA, NHA, NAA', NHacyl, Oacyl, CN, NO₂, SA, SOA, SO₂A, SO₂Ph or SO₃H,
R¹⁰ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by R⁹, and in which one, two or three methylene groups may be replaced by N, O and/or S.
Ar denotes mono- or bicyclic aromatic ring system having 0, 1, 2, 3 or 4 N, O and/or S atoms which is unsubstituted or mono-, di- or trisubstituted by A and/or R⁹,
Ph denotes phenyl which is unsubstituted or mono-, di- or trisubstituted by A,
Hal denotes F, Cl, Br or I, to give a compound of the formula VII

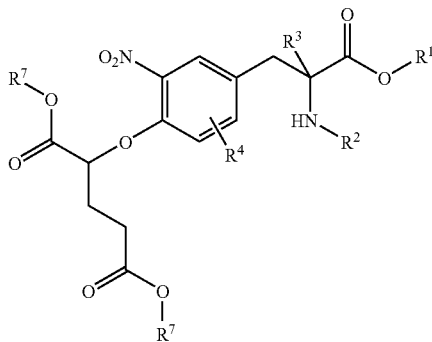

in which
R¹ denotes H, alkyl having 1, 2, 3, 4, 5 or 6 C atoms or benzyl,
R² denotes $R^{10}$, CO—$R^{10}$, COOR⁶, COOR¹⁰, CONHR¹⁰, SO₂R⁶ or SO₂R¹⁰,
R³ denotes H or alkyl having 1-6 C atoms,
R⁴ denotes H, Hal, OA, NHR¹⁰, N(R¹⁰)₂, —NH-acyl, —O-acyl, CN, NO₂, OR¹⁰, SR¹⁰, R² or CONHR¹⁰,
R⁶ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, NO₂, =NH or =O,
R⁷ denotes benzyl or alkyl having 1, 2, 3, 4, 5 or 6 C atoms,
R⁹ denotes H, Hal, OA, NHA, NAA', NHacyl, Oacyl, CN, NO₂, SA, SOA, SO₂A, SO₂Ph or SO₃H,
R¹⁰ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by R⁹ and in which one, two or three methylene groups may be replaced by N, O and/or S.
Ar denotes mono- or bicyclic aromatic ring system having 0, 1, 2, 3 or 4 N, O and/or S atoms which is unsubstituted or mono-, di- or trisubstituted by A and/or R⁹,
Ph denotes phenyl which is unsubstituted or mono-, di- or trisubstituted by A,
Hal denotes F, Cl, Br or I,
d) then a compound of the formula VII is converted into a compound of the formula VIII

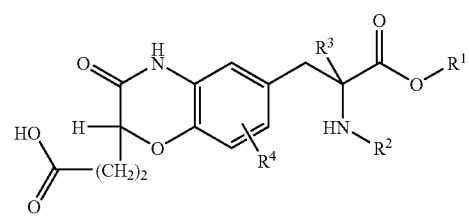

in which
R¹ denotes H, alkyl having 1, 2, 3, 4, 5 or 6 C atoms or benzyl,
R² denotes $R^{10}$, CO—$R^{10}$, COOR⁶, COOR¹⁰, CONHR¹⁰, SO₂R⁶ or SO₂R¹⁰,
R³ denotes H or alkyl having 1-6 C atoms,
R⁴ denotes H, Hal, OA, NHR¹⁰, N(R¹⁰)₂, —NH-acyl, —O-acyl, CN, NO₂, OR¹⁰, SR¹⁰, R² or CONHR¹⁰,
R⁶ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, NO₂, =NH or =O,
R⁹ denotes H, Hal, OA, NHA, NAA', NHacyl, Oacyl, CN, NO₂, SA, SOA, SO₂A, SO₂Ph or SO₃H,
R¹⁰ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by R⁹ and in which one, two or three methylene groups may be replaced by N, O and/or S,
Ar denotes mono- or bicyclic aromatic ring system having 0, 1, 2, 3 or 4 N, O and/or S atoms which is unsubstituted or mono-, di- or trisubstituted by A and/or R⁹,
Ph denotes phenyl which is unsubstituted or mono-, di- or trisubstituted by A,
Hal denotes F, Cl, Br or I,
e) subsequently, if desired, a compound of the formula VIII is converted into a compound of the formula VIIIa

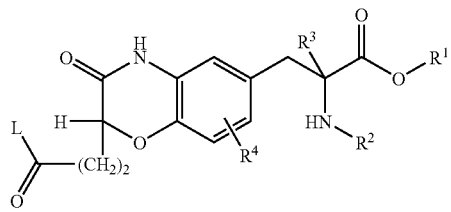

in which
R¹, R², R³ and R⁴ have the meanings indicated under d) and
L denotes Cl, Br, I or a reactively functionally modified OH group,
e) then a compound of the formula VIII or a compound of the formula VIIIa is reacted
e) i) with a compound of the formula IX

R⁵—H   IX in which
R⁵ denotes $NH_2$, $H_2N-C(=NH)$ or $H_2N-(C=NH)-NH$, where the primary amino groups may also be provided with conventional amino-protecting groups, or may be mono-, di- or trisubstituted by $R^{10}$, $CO-R^{11}$, $COOR^{10}$ or $SO_2R^{10}$,
in which $R^{10}$ has the meanings indicated for the formula I, or is reacted e) ii) with a compound of the formula X

R⁶—$NH_2$   X in which
R⁶ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, $NO_2$, =NH or =O, to give a compound of the formula I, subsequently, if desired, a radical R² is converted into another radical R² by reacting a compound of the formula I in which R² denotes H with a compound selected from the group
L-$R^{10}$, L-CO—$R^{10}$, L-COOR⁶, L-COOR¹⁰, $R^{10}$—N=C=O, R⁶—$SO_2L$, $R^{10}$—$SO_2L$, in which
R¹⁰ denotes A, Ar or aralkylene having 7-14 C atoms,
A and Ar have the meanings indicated and
L denotes Cl, Br, I or a free or reactively functionally modified OH group, and/or a base or acid of the formula I is converted into one of its salts.

WO 98/35949 is to be regarded as the closest prior art. The reaction starting from a dibromo compound is carried out therein analogously to the following scheme (Example 8 in WO 98/35949):

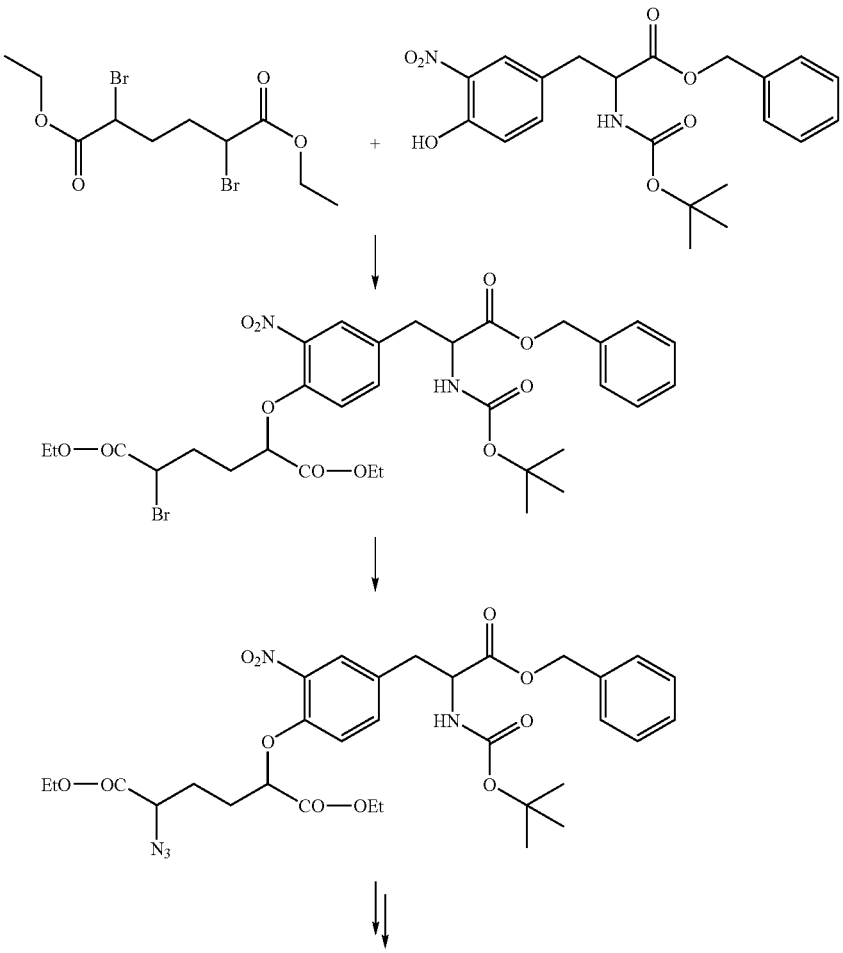

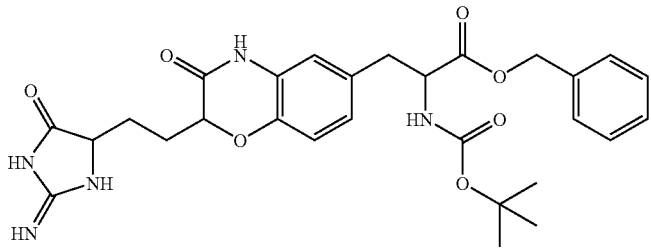
In Example 11 of WO 98/35949, the reaction is carried out analogously to the following scheme:
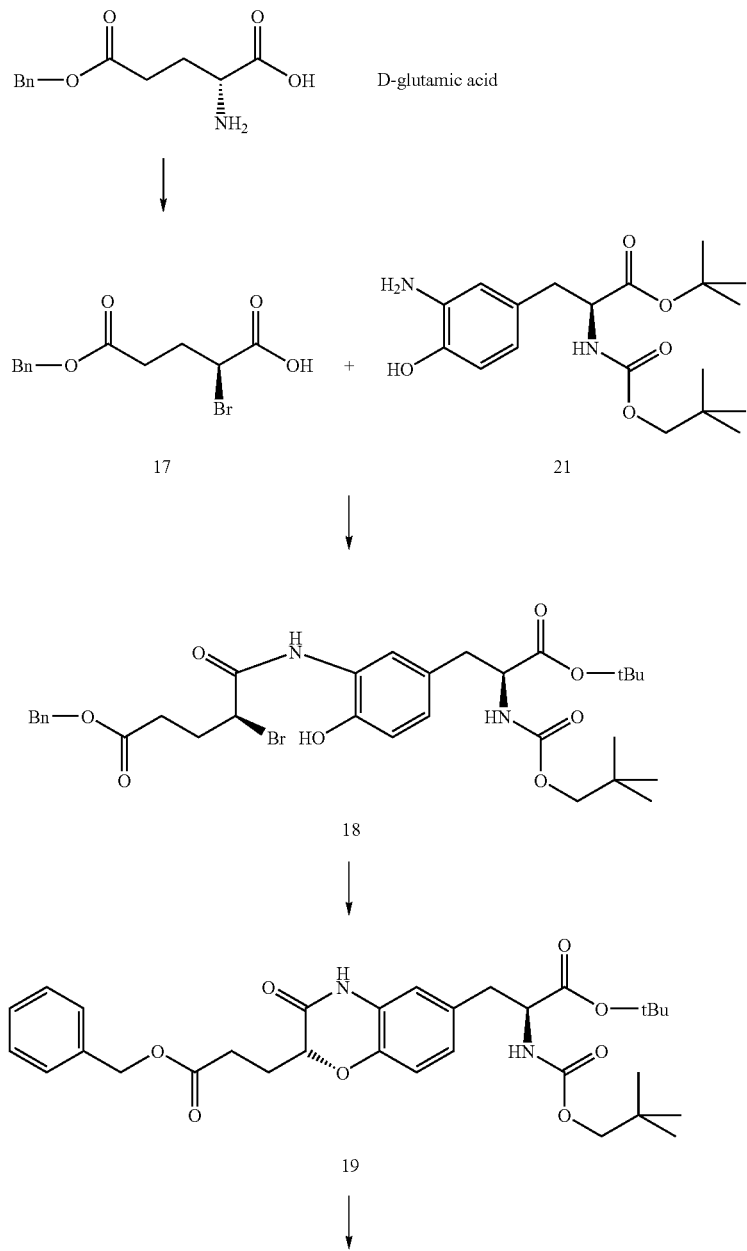

-continued

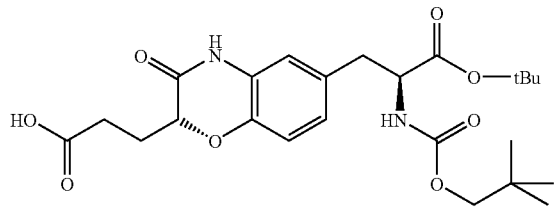

20

In contrast to the processes described in WO 98/35949, the processes according to the invention surprisingly proceed with high stereospecificity, i.e. no racemisation is evident or the selectivity is >96%.

The compounds of the formula I and salts thereof have very valuable pharmacological properties while being well tolerated. In particular, they act as integrin inhibitors, inhibiting, in particular, the interactions of the $\alpha_v$ integrin receptors with ligands. The compounds exhibit particular efficacy in the case of integrins $\alpha_v\beta_3$ and $\alpha_v\beta_5$. The compounds are very particularly effective as adhesion receptor antagonists for the vitronectin receptor $\alpha_{v\beta3}$. This action can be demonstrated, for example, by the method described by J. W. Smith et al. in J. Biol. Chem. 265, 11008-11013 and 12267-12271 (1990).

B. Felding-Habermann and D. A. Cheresh describe in Curr. Opin. Cell. Biol. 5, 864 (1993) the significances of the integrins as adhesion receptors for a very wide variety of phenomena and clinical pictures, especially in relation to the vitronectin receptor $\alpha_v\beta_3$.

The dependence of the occurrence of angiogenesis on the interaction between vascular integrins and extracellular matrix proteins is described by P. C. Brooks, R. A. Clark and D. A. Cheresh in Science 264, 569-71 (1994).

The possibility of inhibiting this interaction and thus initiating apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157-64 (1994).

The experimental evidence that the compounds according to the invention also prevent the attachment of living cells to the corresponding matrix proteins and accordingly also prevent the attachment of tumour cells to matrix proteins can be provided in a cell adhesion test carried out analogously to the method of F. Mitjans et al., J. Cell Science 108, 2825-2838 (1995).

P. C. Brooks et al. in J. Clin. Invest. 96, 1815-1822 (1995) describe $\alpha_v\beta_3$ antagonists for combating cancer and for the treatment of tumour-induced angiogenic diseases.

The compounds of the formula I according to the invention can therefore be employed as medicament active ingredients, in particular for the treatment of tumour diseases, osteoporoses, osteolytic diseases and for suppressing angiogenesis.

Compounds of the formula I which block the interaction of integrin receptors and ligands prevent the spread of tumour cells by metastasis. This is confirmed by the following observations:

The spread of tumour cells from a local tumour into the vascular system takes place through the formation of microaggregates (microthrombi) through interaction of the tumour cells with blood platelets. The tumour cells are masked by the protection in the microaggregate and are not recognised by the cells of the immune system.

The microaggregates are able to attach to vascular walls, simplifying further penetration of tumour cells into the tissue.

Since the formation of the microthrombi is promoted by fibrinogen binding to the fibrinogen receptors on activated blood platelets, the GPIIa/IIIb antagonists can be regarded as effective metastasis inhibitors.

Besides the binding of fibrinogen, fibronectin and the Willebrand factor to the fibrinogen receptor of the blood platelets, compounds of the formula I also inhibit the binding of further adhesive proteins, such as vitronectin, collagen and laminin, to the corresponding receptors on the surface of various cell types. In particular, they prevent the formation of blood platelet thrombi and can therefore be employed for the treatment of thromboses, apoplexy, cardiac infarction, inflammation and arteriosclerosis.

In particular, the compounds of the formula I can also be used in ophthalmology.

The properties of the compounds can also be determined by methods described in EP-A1-0 462 960. The inhibition of the binding of fibrinogen to the fibrinogen receptor can be determined by the method indicated in EP-A1-0 381 033.

The thrombocyte aggregation-inhibiting action can be determined in vitro by the method of Born (Nature 4832, 927-929, 1962).

The invention accordingly relates to compounds of the formula I according to Claim 1 and/or physiologically acceptable salts thereof for the preparation of a medicament for use as integrin inhibitors.

In particular, the invention relates to compounds of the formula I according to Claim 1 and/or acceptable salts thereof in which $R^2$ has the meaning camphor-10-sulfonyl or 2,2-dimethylpropoxycarbonyl, for the preparation of a medicament for combating pathologically angiogenic diseases, tumours, osteoporosis, inflammation and infections.

The compounds of the formula I can be employed as medicament active ingredients in human and veterinary medicine, for the prophylaxis and/or therapy of thrombosis, myocardial infarction, arteriosclerosis, inflammation, apoplexy, angina pectoris, tumour diseases, osteolytic diseases, such as osteoporosis, pathologically angiogenic diseases, such as, for example, inflammation, ophthalmological diseases, diabetic retinopathy, macular degeneration, myopia, ocular histoplasmosis, rheumatic arthritis, osteoarthritis, rubeotic glaucoma, ulcerative colitis, Crohn's disease, atherosclerosis, psoriasis, restenosis after angioplasty, viral infection, bacterial infection, fungal infection, in the case of acute kidney failure and in wound healing for supporting the healing processes.

The compounds of the formula I can be employed as antimicrobially acting substances in operations where biomaterials, implants, catheters or cardiac pacemakers are used. They have an antiseptic action here. The efficacy of the antimicrobial activity can be determined by the method described by P. Valentin-Weigund et al., in Infection and Immunity, 2851-2855 (1988).

The abbreviations mentioned above and below stand for:
Ac acetyl
Bn benzyl
BOC tert-butoxycarbonyl
CBZ or Z benzyloxycarbonyl
DBU 1,8-diazabicyclo[5.4.0]undec-7-ene
DCCl dicyclohexylcarbodiimide
DMF dimethylformamide
DOPA (3,4-dihydroxyphenyl)alanine
DPFN 3,5-dimethylpyrazol-1-formamidinium nitrate
EDCl N-ethyl-N,N'-(dimethylaminopropyl)carbodiimide
Et ethyl
Fmoc 9-fluorenylmethoxycarbonyl
HOBt 1-hydroxybenzotriazole
Me methyl
Mtr 4-methoxy-2,3,6-trimethylphenylsulfonyl
HONSu N-hydroxysuccinimide
POA phenoxyacetyl
TBTU O-(benzotriazol-1-yl)-N,N, N',N'-tetramethyluronium tetrafluoroborate
TFA trifluoroacetic acid
Trt trityl (triphenylmethyl)
Z or CBZ benzyloxycarbonyl.

The compounds of the formula I is also taken to mean the optically active forms (stereoisomers), the enantiomers, the racemates, the diastereomers and the hydrates and solvates of these compounds. Solvates of the compounds is taken to mean adductions of inert solvent molecules onto the compounds which form owing to their mutual attractive force. Solvates are, for example, mono- or dihydrates or alcoholates.

Pharmaceutically usable derivatives is taken to mean, for example, the salts of the compounds according to the invention and also so-called prodrug compounds.

Prodrug derivatives is taken to mean compounds of the formula I which have been modified with, for example, alkyl or acyl groups, sugars or oligopeptides and which are rapidly cleaved in the organism to give the active compounds according to the invention.

These also include biodegradable polymer derivatives of the compounds according to the invention, as described, for example, in Int. J. Pharm. 115, 61-67 (1995).

The compounds of the formula I also encompass mixtures of the compounds of the formula I, for example mixtures of two diastereomers, for example in the ratio 1:1, 1:2, 1:3, 1:4, 1:5, 1:10, 1:100 or 1:1000. These are particularly preferably mixtures of stereoisomeric compounds.

Throughout the invention, all radicals which occur a number of times, such as, for example, A and A', may be identical or different, i.e. are independent of one another.

In the above formulae, alkyl has 1, 2, 3, 4, 5, 6, 7, 8, 9, 10, 11, 12, 13, 14 or 15 C atoms and preferably stands for methyl, ethyl, propyl, isopropyl, butyl, isobutyl, sec-butyl or tert-butyl, furthermore also for pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2-, 1,2,2-trimethylpropyl, heptyl, octyl, nonyl or decyl.

In a preferred embodiment, A denotes unsubstituted alkyl or cycloalkyl having 1, 2, 3, 4, 5, 6, 7, 8, 9, 10, 11, 12, 13, 14 or 15 C atoms. Cycloalkyl preferably denotes cyclopropyl, cyclobutyl, cyclopentyl, cyclohexyl, cycloheptyl or 3-menthyl. In particular, cycloalkyl denotes the radical of a bicyclic terpene, the camphor-10-yl radical is very particularly preferred.

Alkylene preferably denotes methylene, ethylene, propylene, butylene, pentylene, furthermore also hexylene, heptylene, ocytylene, nonylene or decylene.

Aralkylene preferably denotes alkylenephenyl and is, for example, preferably benzyl or phenethyl.

Cycloalkylene preferably denotes cyclopropylene, 1,2- or 1,3-cyclobutylene, 1,2- or 1,3-cyclopentylene, 1,2-, 1,3- or 1,4-cyclohexylene, furthermore 1,2-, 1,3- or 1,4-cycloheptylene.

CO-A is alkanoyl or cycloalkanoyl and preferably denotes formyl, acetyl, propionyl, butyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Acyl is $C_1$-$C_7$-acyl and has 1, 2, 3, 4, 5, 6 or 7 C atoms and preferably denotes, for example, formyl, acetyl, propionyl, butyryl, trifluoroacetyl or benzoyl.

Preferred substituents for alkyl, alkylene, cycloalkyl, cycloalkylene, alkanoyl and cycloalkanoyl are, for example, Hal, OA, NHA, NAA', CN, $NO_2$, SA, SOA, $SO_2A$, $SO_2Ar$ and/or $SO_3H$, in particular, for example, F, Cl, hydroxyl, methoxy, ethoxy, amino, dimethylamino, methylthio, methylsulfinyl, methylsulfonyl or phenylsulfonyl.

Preferred substituents for Ar and arylene are, for example, A and/or Hal, OA, NHA, NAA', CN, $NO_2$, SA, SOA, $SO_2A$, $SO_2Ar$ and/or $SO_3H$, in particular, for example, F, Cl, hydroxyl, methoxy, ethoxy, amino, dimethylamino, methylthio, methylsulfinyl, methylsulfonyl or phenylsulfonyl.

In the radicals alkyl, alkylene, cycloalkyl, cycloalkylene, alkanoyl and cycloalkanoyl, in each case one, two or three methylene groups may be replaced by N, O and/or S.

Ar—CO is aroyl and preferably denotes benzoyl or naphthoyl.

Ar is unsubstituted, preferably—as indicated—monosubstituted phenyl, in detail preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-methylthiophenyl, o-, m- or p-methylsulfinylphenyl, o-, m- or p-methylsulfonylphenyl, o-, m- or p-aminophenyl, o-, m- or p-methylaminophenyl, o-, m- or p-dimethylaminophenyl, o-, m- or p-nitrophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, 2,5-dimethylphenyl, p-iodophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl, 2,4,6-triisopropylphenyl, naphthyl, 1,3-benzodioxol-5-yl, 1,4-benzodioxan-6-yl, benzothiadiazol-5-yl or benzoxadiazol-5-yl.

Furthermore, Ar preferably denotes 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

Arylene has the same meanings as indicated for Ar, with the proviso that a further bond from the aromatic system to the closest bond neighbour has been formed.

Heterocycloalkylene preferably denotes 1,2-, 2,3- or 1,3-pyrrolidinyl, 1,2-, 2,4-, 4,5- or 1,5-imidazolidinyl, 1,2-, 2,3-, or 1,3-pyrazolidinyl, 2,3-, 3,4-, 4,5- or 2,5-oxazolidinyl, 1,2-, 2,3-, 3,4- or 1,4-isoxazolidinyl, 2,3-, 3,4-, 4,5- or 2,5-thiazolidinyl, 2,3-, 3,4-, 4,5- or 2,5-isothiazolidinyl, 1,2-, 2,3-, 3,4- or 1,4-piperidinyl, 1,4- or 1,2-piperazinyl, furthermore preferably 1,2,3-tetrahydrotriazol-1,2- or -1,4-yl, 1,2,4-tetrahydrotriazol-1,2- or 3,5-yl, 1,2- or 2,5-tetrahydrotetrazolyl, 1,2,3-tetrahydrooxadiazol-2,3-, -3,4-, -4,5- or -1,5-yl, 1,2,4-tetrahydrooxadiazol-2,3-, -3,4- or -4,5-yl, 1,3,4-tetrahydrothiadiazol-2,3-, -3,4-, -4,5- or -1,5-yl, 1,2,4-tetrahydrothiadiazol-2,3-, -3,4-, -4,5- or -1,5-yl, 1,2,3-thiadiazol-2,3-, -3,4-, -4,5- or -1,5-yl, 2,3- or 3,4-morpholinyl, 2,3-, 3,4- or 2,4-thiomorpholinyl.

$R^6$ is a mono- or bicyclic saturated, unsaturated or aromatic heterocycle, preferably 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

The heterocyclic radicals may also be partially or fully hydrogenated. $R^6$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The said heterocyclic rings may also be mono-, di- or trisubstituted by Hal, A, —CO-A, OA, CN, COOH, COOA, CONHA, $NO_2$, =NH or =O.

$R^6$ particularly preferably denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl, 1H-imidazol-2-yl is very particularly preferred.

$R^3$ preferably denotes H.
$R^4$ preferably denotes H.
$R^9$ preferably denotes H.
$R^{10}$ preferably denotes H, alkyl having 1, 2, 3, 4, 5 or 6 C atoms, camphor-10-yl or benzyl.

In the process according to the invention, in step b), in the compounds of the formula IV and V,
$R^8$ preferably denotes methylsulfonyl, trifluoromethylsulfonyl, phenylsulfonyl or p-tolylsulfonyl.

Accordingly, the invention relates, in particular, to the processes for the preparation of compounds of the formula I in which at least one of the said radicals has one of the preferred meanings indicated above. Some preferred groups of compounds which are prepared by the process according to the invention can be expressed by the following sub-formulae Ia to If, which conform to the formula I and in which the radicals not designated in greater detail have the meaning indicated for the formula I, but in which in Ia) $R^3$ denotes H and $R^4$ denotes H;
in Ib) $R^6$ denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl;
in Ic) $R^9$ denotes H;
in Id) $R^{10}$ denotes H, alkyl having 1, 2, 3, 4, 5 or 6 C atoms, camphor-10-yl or benzyl;
in Ie) A denotes unsubstituted alkyl or cycloalkyl having 1-15 C atoms,
in If) A denotes alkyl having 1, 2, 3, 4, 5 or 6 C atoms, $R^{10}$ denotes H, alkyl having 1, 2, 3, 4, 5 or 6 C atoms, camphor-10-yl or benzyl,
and pharmaceutically usable derivatives, solvates and stereoisomers thereof.

Preference is given to a process for the preparation of compounds of the formula I in which
$R^1$ denotes H, alkyl having 1, 2, 3, 4, 5 or 6 C atoms or benzyl,
$R^2$ denotes $R^{10}$, CO—$R^{10}$, COO$R^{10}$ or $SO_2R^{10}$,
$R^3$ denotes H,
$R^4$ denotes H,
$R^5$ denotes $R^6$,
$R^6$ denotes a mono- or bicyclic saturated, unsaturated or aromatic heterocycle having 1 to 4 N, O and/or S atoms, which may be unsubstituted or mono-, di- or trisubstituted by Hal, A, —CO-A, OA, CN, COOH, COOA, CONHA, $NO_2$, =NH or =O,
X denotes NH,
$R^{10}$ denotes H, alkyl having 1, 2, 3, 4, 5 or 6 C atoms, camphor-10-yl or benzyl, A denotes alkyl having 1, 2, 3, 4, 5 or 6 C atoms,
Hal denotes F, Cl, Br or I, and pharmaceutically usable derivatives, solvates and stereoisomers thereof.

In the last-mentioned preferred embodiment, $R^6$ preferably denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl.

Preference is furthermore given to a process for the preparation of compounds of the formula Ia

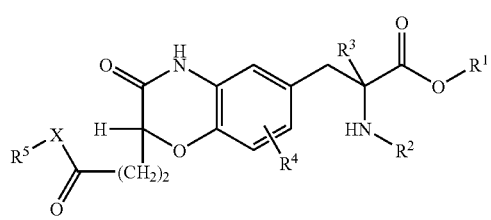

Ia in which
$R^1$ denotes H or alkyl having 1, 2, 3 or 4 C atoms,
$R^2$ denotes $R^{10}$, CO—$R^{10}$, COOR$^{10}$ or SO$_2$R$^{10}$,
$R^3$ denotes H,
$R^4$ denotes H,
$R^5$ denotes $R^6$,
X denotes NH,
$R^6$ denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl,
$R^{10}$ denotes H or alkyl having 1, 2, 3, 4, 5 or 6 C atoms and
A denotes alkyl having 1, 2, 3, 4, 5 or 6 C atoms, and pharmaceutically usable derivatives, solvates and stereoisomers thereof, where
a) 5-oxotetrahydrofuran-2-carboxylic acid is reacted with a compound of the formula II $R^7$-L    II in which
$R^7$ denotes benzyl or alkyl having 1, 2, 3, 4, 5 or 6 C atoms and
L denotes Cl, Br, I or a free or reactively functionally modified OH group, to give a compound of the formula III

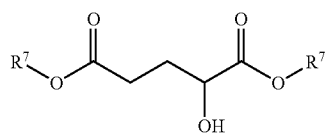

III in which
$R^7$ denotes benzyl or alkyl having 1, 2, 3, 4, 5 or 6 C atoms,
b) then a compound of the formula III is reacted with a compound of the formula IV $R^8$-L    IV in which
$R^8$ denotes alkylsulfonyl having 1-6 C atoms or arylsulfonyl having 6-10 C atoms and
L denotes Cl, Br, I or a free or reactively functionally modified OH group, to give a compound of the formula V

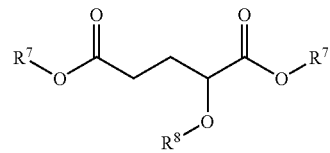

V in which
$R^7$ denotes benzyl or alkyl having 1, 2, 3, 4, 5 or 6 C atoms and
$R^8$ denotes alkylsulfonyl having 1-6 C atoms or arylsulfonyl having 6-10 C atoms,
c) then a compound of the formula III or V is reacted with a compound of the formula VI

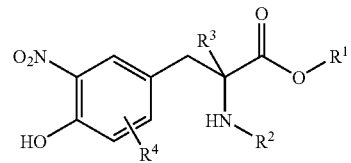

VI in which
$R^1$ denotes H or alkyl having 1, 2, 3 or 4 C atoms,
$R^2$ denotes $R^{10}$, CO—$R^{10}$, COOR$^{10}$ or SO$_2$R$^{10}$,
$R^3$ denotes H,
$R^4$ denotes H,
$R^{10}$ denotes H or alkyl having 1, 2, 3, 4, 5 or 6 C atoms and, to give a compound of the formula VII

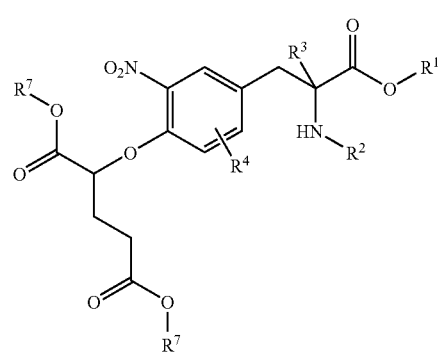

VII in which
$R^1$ denotes H or alkyl having 1, 2, 3 or 4 C atoms,
$R^2$ denotes $R^{10}$, CO—$R^{10}$, COOR$^{10}$ or SO$_2$R$^{10}$,
$R^3$ denotes H,
$R^4$ denotes H,
$R^7$ denotes benzyl or alkyl having 1, 2, 3, 4, 5 or 6 C atoms,
$R^{10}$ denotes H or alkyl having 1, 2, 3, 4, 5 or 6 C atoms, d) then a compound of the formula VII is converted into a compound of the formula VIII

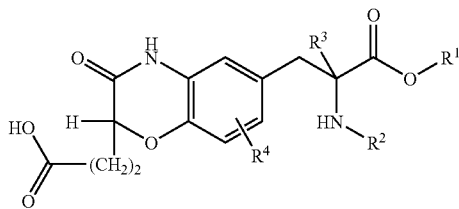

in which
R¹ denotes H or alkyl having 1, 2, 3 or 4 C atoms,
R² denotes $R^{10}$, CO—$R^{10}$, COO$R^{10}$ or SO$_2$$R^{10}$,
R³ denotes H,
R⁴ denotes H,
$R^{10}$ denotes H or alkyl having 1, 2, 3, 4, 5 or 6 C atoms,
e) then a compound of the formula VIII
is reacted with a compound of the formula X $R^6$—NH$_2$X in which
R⁶ denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl, to give a compound of the formula Ia, subsequently, if desired, a radical R² is converted into another radical R² by reacting a compound of the formula Ia in which R² denotes H with a compound selected from the group
L-$R^{10'}$, L-CO—$R^{10'}$, L-COO$R^{10'}$, $R^{10'}$—SO$_2$L, in which
$R^{10'}$ denotes alkyl having 1, 2, 3, 4, 5 or 6 C atoms and
L denotes Cl, Br, I or a free or reactively functionally modified OH group, and/or a base or acid of the formula Ia is converted into one of its salts.

The invention furthermore relates to a process for the preparation of (S)-2-(2,2-dimethylpropoxycarbonylamino)-3-{(S)-2-[2-(1H-imidazol-2-ylcarbamoyl)ethyl]-3-oxo-3,4-dihydro-2H-benzo[1,4]oxazin-6-yl}propionic acid, where
a) (S)-3-nitrotyrosine ethyl ester tosylate is reacted with 2,2-dimethylpropyl chloroformate to give ethyl (S)-2-(2,2-dimethylpropoxycarbonylamino)-3-(4-hydroxy-3-nitrophenyl)propionate 12,
b) 12 is reacted with dibenzyl 2-hydroxypentanedicarboxylate to give dibenzyl (R)-2-{4-[(S)-2-(2,2-dimethylpropoxycarbonyl amino)-2-ethoxycarbonylethyl]-2-nitrophenoxy}pentanedicarboxylate 13,
c) 13 is cyclised to give ethyl (2S)-3-[(2S)-2-(2-carboxyethyl)-3-oxo-3,4-dihydro-2H-benzo[1,4]oxazin-6-yl]-2-(2,2-dimethyl propoxycarbonylamino)propionate 14,
d) 14 is reacted with 2-aminoimidazole to give ethyl 2-(S)-(2,2-di methylpropoxycarbonylamino)-3-{3-oxo-2-(S)-[2-(1H-imidazol-2-ylcarbamoyl)ethyl]-3,4-dihydro-2H-benzo[1,4]oxazin-6-yl}propionate 15 and
e) 15 is converted by ester cleavage into (S)-2-(2,2-dimethylpropoxycarbonylamino)-3-{(S)-2-[2-(1H-imidazol-2-ylcarbamoyl)ethyl]-3-oxo-3,4-dihydro-2H-benzo[1,4]oxazin-6-yl}propionic acid 16.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxyalkanoyl, such as POA; alkoxycarbonyl, such as methoxycarbonyl, ethoxycarbonyl, 2,2,2-trichloroethoxycarbonyl, BOC, 2-iodoethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

The amino-protecting group is cleaved off—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5N HCl in dioxane at 15-30°, the FMOC group can be cleaved off using an approximately 5 to 50% solution of dimethylamine, diethylamine or piperidine in DMF at 15-30°.

Protecting groups which can be removed hydrogenolytically (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

In the compounds of the formula II, IV, and in the compounds selected from the groups L-$R^{10}$, L-CO—$R^{10}$, L-COO$R^6$, L-COO$R^{10}$, $R^{10}$—N=C=O, $R^6$—$SO_2$L, $R^{10}$—$SO_2$L (step e) ii)) or L-$R^{10'}$, L-CO—$R^{10'}$, L-COO$R^6$, L-COO$R^{10'}$, $R^{10'}$—N=C=O, $R^6$—$SO_2$L, $R^{10'}$—$SO_2$L, L preferably denotes Cl, Br, I or a free or reactively modified OH group, such as alkylsulfonyloxy having 1-6 C atoms (preferably methylsulfonyloxy) or arylsulfonyloxy having 6-10 C atoms (preferably phenyl- or p-tolylsulfonyloxy).

The reaction of 5-oxotetrahydrofuran-2-carboxylic acid with a compound of the formula II to give a compound of the formula III is generally carried out in an inert solvent, in the presence of an acid-binding agent, preferably an organic base, such as triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, water, or mixtures of the said solvents.

The reaction of a compound of the formula III with a compound of the formula IV to give a compound of the formula V is generally carried out in an inert solvent, in the presence of an acid-binding agent, in an inert solvent and at temperatures as described for the reaction of 5-oxotetrahydrofuran-2-carboxylic acid with a compound of the formula II.

If the further reaction is carried out by reaction of a compound of the formula V with a compound of the formula VI to give a compound of the formula VII, this reaction is generally carried out in an inert solvent, in the presence of an acid-binding agent, in an inert solvent and at temperatures as described for the reaction of 5-oxotetrahydrofuran-2-carboxylic acid with a compound of the formula II.

If, alternatively, the further reaction is carried out by reaction of a compound of the formula III with a compound of the formula VI to give a compound of the formula VII, this is carried out under conditions of the Mitsunobu reaction, which are known to the person skilled in the art for this reaction.

The conversion of a compound of the formula VII into a compound of the formula VIII is carried out, if $R^7$ denotes benzyl, preferably hydrogenolytically under conditions as described above. The reduction of the nitro group and the cleaving-off of the benzyl groups with cyclisation take place here.

Alternatively, the conversion of a compound of the formula VII into a compound of the formula VIII is carried out
a) by reduction of the nitro group, subsequent ester cleavage and cyclisation or
b) by ester cleavage, subsequent reduction of the nitro group and cyclisation.

An ester cleavage takes place under standard conditions. This is advantageously carried out by solvolysis or hydrogenolysis, as indicated above, for example using NaOH or KOH in dioxane/water at temperatures between 0 and 60° C., preferably between 10 and 40° C.

The reaction of a compound of the formula VIII or VIIIa with a compound of the formula IX or X to give a compound of the formula I is generally carried out in an inert solvent, in the presence of an acid-binding agent, in an inert solvent and at temperatures as described for the reaction of 5-oxotetrahydrofuran-2-carboxylic acid with a compound of the formula II.

In the compounds of the formula VIIIa, L preferably denotes Cl, Br, I or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;). Activated esters are advantageously formed in situ, for example by addition of HOBt or N-hydroxysuccinimide.

If desired, a radical $R^2$ in a compound of the formula I is converted into another radical $R^2$. This is preferably carried out with compounds of the formula I in which $R^2$ denotes H. The reaction is carried out with a compound selected from the group
L-$R^{10}$, L-CO—$R^{10}$, L-COO$R^6$, L-COO$R^{10}$, $R^{10}$—N=C=O, $R^6$—$SO_2$L, $R^{10}$—$SO_2$L in which
$R^{10}$ denotes A, Ar or aralkylene having 7-14 C atoms,
A and Ar have the meanings indicated in Claim 1 and L denotes Cl, Br, I or a free or reactively functionally modified OH group. The reaction is generally carried out in an inert solvent, in the presence of an acid-binding agent, in an inert solvent and at temperatures as described for the reaction of 5-oxotetrahydrofuran-2-carboxylic acid with a compound of the formula II.

The conversion of a cyano group into an amidino group is carried out by reaction with, for example, hydroxylamine and subsequent reduction of the N-hydroxyamidine using hydrogen in the presence of a catalyst, such as, for example, Pd/C.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, an acid of the formula I can be converted into one of its physiologically acceptable metal or ammonium salts by reaction with a base. Possible salts here are, in particular, the sodium, potassium, magnesium, calcium and ammonium salts, furthermore substituted ammonium salts, for example the dimethyl-, diethyl- or diisopropylammonium salts, monoethanol-, diethanol- or diisopropylammonium salts, cyclohexyl-, dicyclohexylammonium salts, dibenzylethylenediammonium salts, furthermore, for example, salts with arginine or lysine.

The compounds of the formula I contain one or more chiral centres and can therefore exist in racemic or optically active form. The racemates obtained can be resolved into the enantiomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture, for example in the volume ratio 82:15:3.

It is of course also possible to obtain optically active compounds of the formula I by the methods described above by using starting materials which are already optically active.

The invention furthermore relates to the intermediate compounds of the formula VII

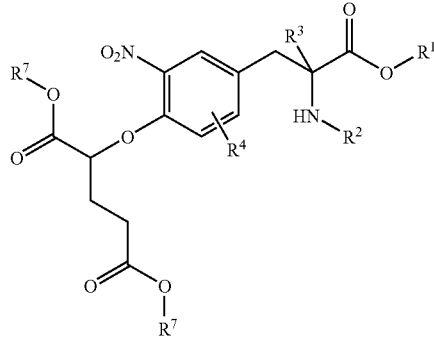

VII in which
$R^1$ denotes H or alkyl having 1, 2, 3 or 4 C atoms,
$R^2$ denotes $R^{10}$, CO—$R^{10}$, COOR$^{10}$ or SO$_2$R$^{10}$,
$R^3$ denotes H.
$R^4$ denotes H,
$R^7$ denotes benzyl or alkyl having 1, 2, 3, 4, 5 or 6 C atoms, $R^9$ denotes H, Hal, OA, NHA, NAA', NHacyl, Oacyl, CN, NO$_2$, SA, SOA, SO$_2$A, SO$_2$Ph or SO$_3$H,
$R^{10}$ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by $R^9$ and in which one, two or three methylene groups may be replaced by N, O and/or S.
Ar denotes mono- or bicyclic aromatic ring system having 0, 1, 2, 3, or 4 N, O and/or S atoms, which is unsubstituted or mono-, di- or trisubstituted by A and/or $R^9$, and salts, solvates and stereoisomers thereof.

Preference is furthermore given to the intermediate compounds of the formula VII

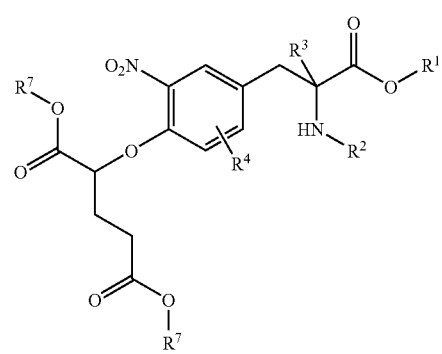

VII in which
$R^1$ denotes H or alkyl having 1, 2, 3 or 4 C atoms,
$R^2$ denotes $R^{10}$, CO—$R^{10}$, COOR$^{10}$ or SO$_2$R$^{10}$,
$R^3$ denotes H,
$R^4$ denotes H,
$R^7$ denotes benzyl or alkyl having 1, 2, 3, 4, 5 or 6 C atoms,
$R^{10}$ denotes H or alkyl having 1, 2, 3, 4, 5 or 6 C atoms, and salts, solvates and stereoisomers thereof.

In addition, the invention relates to a process for the preparation of compounds of the formula VII, and salts, solvates and stereoisomers thereof, in which
a) 5-oxotetrahydrofuran-2-carboxylic acid is reacted with a compound of the formula II $R^7$—L    II where
$R^7$ denotes benzyl or alkyl having 1, 2, 3, 4, 5 or 6 C atoms and
L denotes Cl, Br, I or a free or reactively functionally modified OH group, to give a compound of the formula III

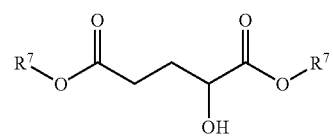

III in which
$R^7$ denotes benzyl or alkyl having 1, 2, 3, 4, 5 or 6 C atoms, b) then a compound of the formula III is reacted with a compound of the formula IV

R$^8$—L    IV in which
R$^8$ denotes alkylsulfonyl having 1-6 C atoms or arylsulfonyl having 6-10 C atoms and
L denotes Cl, Br, I or a free or reactively functionally modified OH group, to give a compound of the formula V

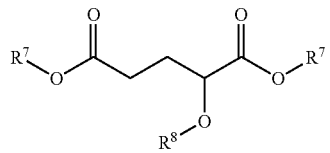

in which
R$^7$ denotes benzyl or alkyl having 1, 2, 3, 4, 5 or 6 C atoms and
R$^8$ denotes alkylsulfonyl having 1-6 C atoms or arylsulfonyl having 6-10 C atoms,
c) then a compound of the formula III or V is reacted with a compound of the formula VI

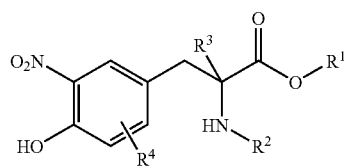

in which
R$^1$ denotes H or alkyl having 1, 2, 3 or 4 C atoms,
R$^2$ denotes R$^{10}$, CO—R$^{10}$, COOR$^{10}$ or SO$_2$R$^{10}$,
R$^3$ denotes H,
R$^4$ denotes H,
R$^9$ denotes H, Hal, OA, NHA, NAA', NHacyl, Oacyl, CN, NO$_2$, SA, SOA, SO$_2$A, SO$_2$Ph or SO$_3$H,
R$^{10}$ denotes H, A, Ar or aralkylene having 7-14 C atoms,
A, A' each, independently of one another, denote H or alkyl or cycloalkyl having 1-15 C atoms, each of which is unsubstituted or mono-, di- or trisubstituted by R$^9$ and in which one, two or three methylene groups may be replaced by N, O and/or S.
Ar denotes mono- or bicyclic aromatic ring system having 0, 1, 2, 3 or 4 N, O and/or S atoms which is unsubstituted or mono-, di- or trisubstituted by A and/or R$^9$, to give a compound of the formula VII, and/or an acid of the formula VII is converted into one of its salts.

The reactions are carried out analogously to the conditions as described for the preparation of the compounds of the formula I.

Above and below, all temperatures are indicated in ° C. In the following examples, "conventional work-up" means: if necessary, water is added, the pH is set to values between 2 and 10, depending on the constitution of the end product, are set, if necessary, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS): EI (electron impact ionisation) M$^+$

FAB (fast atom bombardment) (M+H)$^+$

EXAMPLE 1

The preparation of ethyl 2-(S)-amino-3-{3-oxo-2-(R)-[2-(1H-imidazol-2-ylcarbamoyl)ethyl]-3,4-dihydro-2H-benzo[1,4]oxazin-6-yl}propionate hydrochloride (6) is carried out analogously to the following scheme:

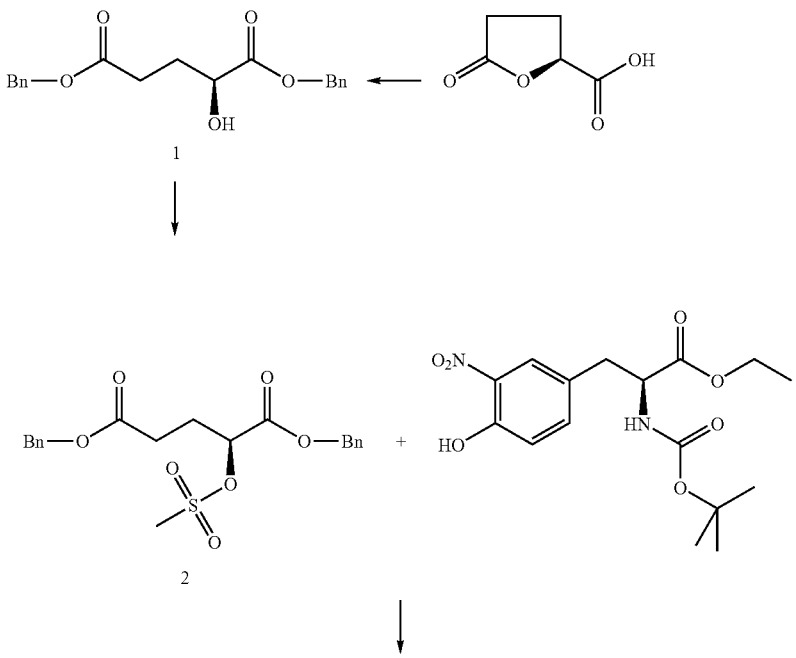

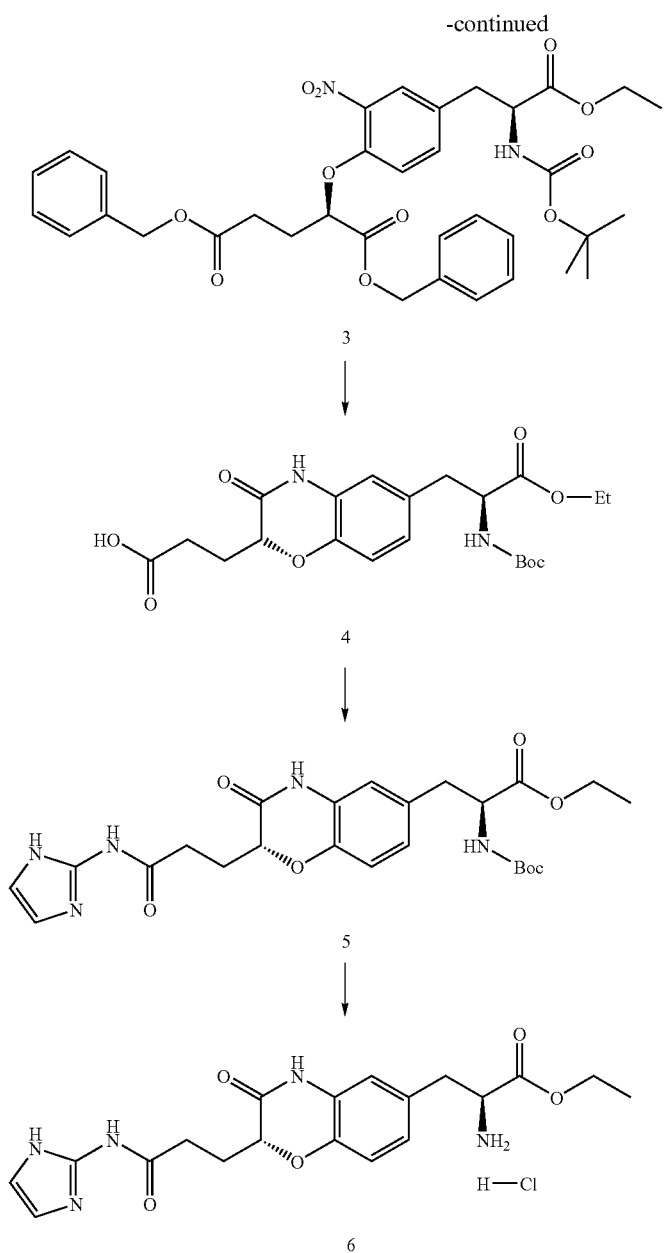

1.1 Dibenzyl (S)-2-hydroxypentanedicarboxylate 1

300 g of caesium carbonate are added to a solution of 100 g of (S)-5-oxofuran-2-carboxylic acid in 1 l of water. The mixture is heated under reflux and stirred for 18 hours. The water is removed, and the residue is dissolved in 750 ml of methanol. 200 g of silica gel are added, and the mixture is stirred for 15 minutes. The solvent is removed, giving the biscaesium salt on silica gel as a white powder, which is dried for 18 hours at 60° under reduced pressure.

The crude product is suspended in 1 l of absolute DMF, 183 ml of benzyl bromide are added, and the mixture is stirred at room temperature for 16 hours.

When the reaction is complete (HPLC check), the silica gel is separated off by filtration, and the solution is poured into 2 l of water. Conventional work-up gives 1 as oil.

Yield: 237 g (94%) HPLC (Chromolith™ Performance RP-18e, eluent: gradient system, water+0.1% of TFA/acetonitrile+0.1% of TFA 99:1→1:99 in 10 min, 3 ml/min) $R_t$=5.25 min Chiral HPLC (Chiralcel OD-H, 250 mm, heptane/ethanol 85:15, 0.8 ml/min): $R_t$=12.95 min ESI-MS: $M^{+1}$=329

$^1$H-NMR (400 MHz, DMSO): corresponds $[\alpha]_D$=−9.6° (c=1.1 in ethanol).

1.2 Dibenzyl (S)-2-methanesulfonyloxypentanedicarboxylate 2

500 ml of triethylamine are added to a solution of 236.9 g of 1 in 1.2 l of dichloromethane. With ice cooling, a solution of 83.6 ml of methanesulfonyl chloride in 200 ml of dichloromethane is added. The mixture is stirred at 5-100 for 30 minutes, the precipitated triethylamine hydrochloride is removed, and the product is subjected to conventional work-up, giving 2 as oil.

Yield: 277 g (94%) HPLC (Chromolith™ Performance RP-18e, eluent gradient system: water+0.1% of TFA/acetonitrile+0.1% of TFA 99:1→1:99 in 10 min, 3 ml/min) $R_t$=5.92 min DC: Si-60, toluene/acetone 9:1, $R_f$=0.5 ESI-MS: $M^{+1}$=407 $[\alpha]_D$=−31.1° (c=1.01 in chloroform).

1.3 Dibenzyl 2-(R)-[4-(2-(S)-tert-butoxycarbonylamino-2-ethoxycarbonylethyl)-2-nitrophenoxy]pentanedicarboxylate 3

174.1 g of potassium carbonate are added to a solution of 178.6 g of N-Boc-L-tyrosine ethyl ester and 257 g of 2 in 1.25 l of acetonitrile, and the mixture is heated under reflux for 16 hours. After the insoluble salts have been separated off, the mixture is subjected to conventional work-up, giving 3.

Yield: 369 g (99%) HPLC (Chromolith™ Performance RP-18e, eluent gradient system: water+-0.1% of TFA/acetonitrile+0.1% of TFA 99:1→1:99 in 10 min, 3 ml/min) $R_t$=7.04 min, purity 90%. Chiral HPLC: (Chiralpak™ AD, 250 mm, heptane/isopropanol 60:40, 0.8 ml/min) $R_t$=27.23 min, purity=96.6% (de [diastereomeric excess]=93.2%) DC: Si-60, toluene/acetone 9:1, Rf=0.38 ESI-MS: $M^{+1}$=665 $[\alpha]_D$=−35.8° (c=1.02 in ethanol).

1.4 Ethyl 2-(S)-tert-butoxycarbonylamino-3-[2-(R)-(2-carboxyethyl)-3-oxo-3,4-dihydro-2H-benzo[1,4]oxazin-6-yl]propionate 4

Hydrogen is passed through a solution of 369 g of 3 in 2.6 l of acetic acid at 600 in the presence of 95 g of palladium (5% on activated carbon) for 6 hours. Removal of the catalyst and conventional work-up gives 4.

Yield: 164 g (75%) HPLC (Chromolith™ Performance RP-18e, eluent gradient system: water+0.1% of TFA/acetonitrile+0.1% of TFA 99:1→1:99 in 10 min, 3 ml/min) $R_t$=4.51 min. DC: Si-60, dichloromethane/methanol 9:1, Rf=0.35 ESI-MS: $M^{+1}$=437 $[\alpha]_D$=+14.0° (c=1.0 in methanol)

m.p. 154-158°.

1.5 Ethyl 2-(S)-tert-butoxycarbonylamino-3-{3-oxo-2-(R)-[2-(1H-imidazol-2-ylcarbamoyl)ethyl]-3,4-dihydro-2H-benzo[1,4]oxazin-6-yl}propionate 5

128.54 g of potassium carbonate are added to a solution of 163 g of 4, 74 g of 2-aminoimidazole sulfate, 155.7 g of TBTU and 15.13 g of HOBt in 1.2 l of absolute DMF, and the mixture is stirred at 700 under nitrogen for 16 hours. A further 25 g of 2-aminoimidazole sulfate, 51 g of TBTU, 5 g of HOBt and 26 g of potassium carbonate are added, and the mixture is stirred for a further 5 hours. The insoluble salts are separated off, the DMF is removed, and the residue is poured into 3 l of ice-water. The precipitate is separated off, washed with water and dried in air. Recrystallisation from ethanol gives 5.

Yield: 125 g (67%) HPLC (Chromolith™ Performance RP-18e, eluent gradient system: water+0.1% of TFA/acetonitrile+0.1% of TFA 99:1→1:99 in 10 min, 3 ml/min) $R_t$=4.13 min. Chiral HPLC: (Chiralpak™ AD, 250 mm, heptane/ethanol 40:60, 0.8 ml/min) $R_t$=16.21 min, purity=96.6% (de=93.2%) DC: Si-60, dichloromethane/methanol 9:1, Rf=0.28 ESI-MS: $M^{+1}$=502 $[\alpha]_D$=+17.3° (c=1.04 in DMSO)

m.p. 215° C. (decomposition).

1.6 Ethyl 2-(S)-amino-3-{3-oxo-2-(R)-[2-(1H-imidazol-2-ylcarbamoyl)ethyl]-3,4-dihydro-2H-benzo[1,4]oxazin-6-yl}propionate, hydrochloride 6

0.9 l of a 4.5 M solution of HCl in dioxane is added to a suspension of 112 g of 5 in 1 of dioxane, and the mixture is stirred for a further 16 hours.

The precipitate is separated off, washed with a little dioxane and 3× with petroleum ether. Drying under reduced pressure gives 6 as white product.

Yield: 112.6 g (quant.)

HPLC (Chromolith™ Performance RP-18e, eluent gradient system: water+0.1% of TFA/acetonitrile+0.1% of TFA 99:1→1:99 in 10 min, 3 ml/min) $R_t$=2.67 min. ESI-MS: $M^{+1}$=402 m.p. 220° (decomposition)

$[\alpha]_D$=+34.10 (c=1.0 in water).

Analogous reaction of
ethyl 2-(S)-tert-butoxycarbonyl amino-3-[2-(R)-(2-carboxyethyl)-3-oxo-3,4-dihydro-2H-benzo[1,4]oxazin-6-yl]propionate 4 with
2-aminobenzimidazole gives the compound
ethyl 2-(S)-tert-butoxycarbonyl amino-3-{3-oxo-2-(R)-[2-(1H-benzimidazol-2-ylcarbamoyl)ethyl]-3,4-dihydro-2H-benzo[1,4]oxazin-6-yl}-propionate 5-a.

EXAMPLE 2

The preparation of (S)-2-(2,2-dimethylpropoxycarbonylamino)-3-{(R)-2-[2-(1H-imidazol-2-ylcarbamoyl)ethyl]-3-oxo-3,4-dihydro-2H-benzo[1,4]oxazin-6-yl}propionic acid, sodium salt (11) is carried out analogously to the following scheme:

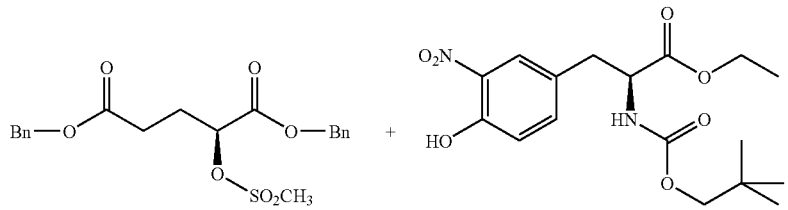

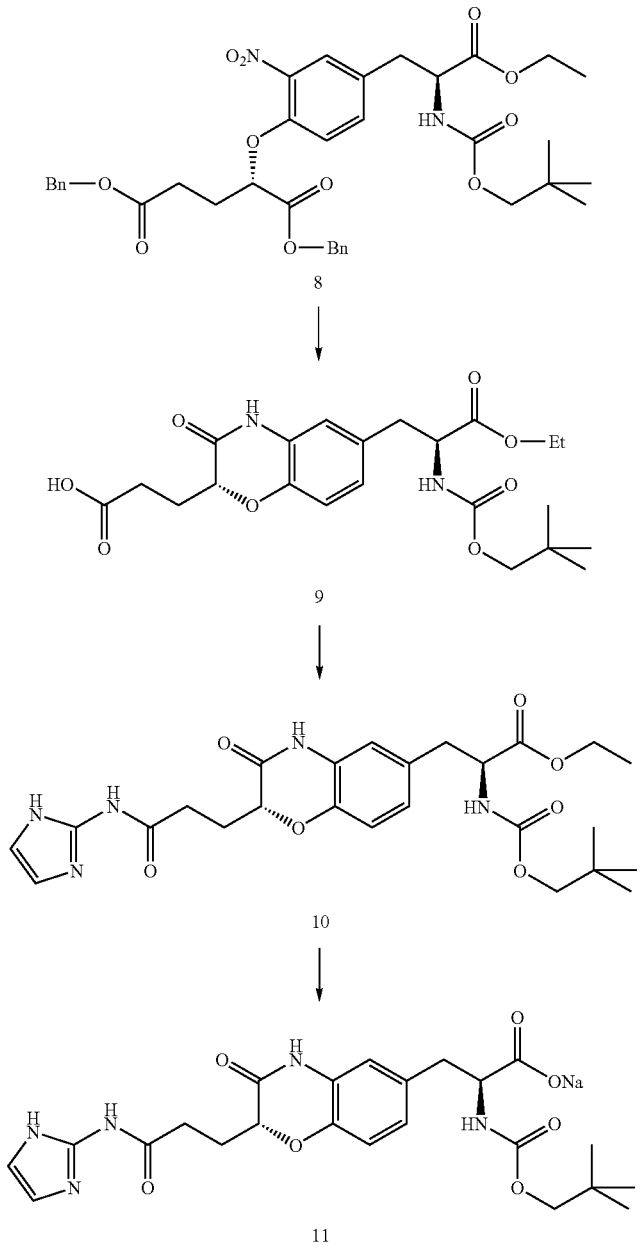

2.1 Ethyl (S)-2-(2,2-dimethylpropoxycarbonylamino)-3-(4-hydroxy-3-nitrophenyl)propionate 7

81.32 g of NaHCO$_3$ are added in small portions to a suspension of 206.4 g of L-3-nitrotyrosine ethyl ester tosylate in 750 ml of water and 250 ml of THF. A solution of 60 ml of 2,2-dimethylpropyl chloroformate in 250 ml of THF is subsequently added dropwise, and the mixture is stirred at room temperature for a further 2 hours. After removal of the THF, the mixture is subjected to conventional work-up. The crystallised product 7 is washed with petroleum ether and dried under reduced pressure.

Yield: 107 g (72%) HPLC (Chromolith™ Performance RP-18e, eluent gradient system: water+0.1% of TFA/acetonitrile+0.1% of TFA 99:1→1:99 in 10 min, 3 ml/min) R$_t$=5.68 min. DC: Si-60, toluene/acetone 9:1, Rf=0.42 ESI-MS: M$^{+1}$=369 [α]$_D$=+0.9° (c=1.03 in methanol) m.p. 64-67°.

2.2 Dibenzyl (S) 2-{4-[(S)-2-(2,2-dimethylpropoxycarbonylamino)-2-ethoxycarbonylethyl]-2-nitrophenoxy}pentanedicarboxylate 8

9.24 g of K$_2$CO$_3$ are added to a solution of 9.85 g of 7 in 100 ml of acetonitrile. A solution of 16.3 g of the mesylate 2 in 50 ml of acetonitrile is then added dropwise, and the mixture is stirred under reflux (bath temperature 80°) for 16 hours.

The mixture is cooled to room temperature, the insoluble salts are separated off, the solvent is removed, the residue is dissolved in 200 ml of ethyl acetate and subjected to conventional work-up, giving 8 as yellow syrup.

Yield: 23 g (75% purity, still contains mesylate) HPLC (Chromolith™ Performance RP-18e, eluent gradient system: water+0.1% of TFA/acetonitrile+0.1% of TFA 99:1→1:99 in 10 min, 3 ml/min) $R_t$=7.17 min. Chiral HPLC: (Chiralpak™ AD, 250 mm, heptane/isopropanol 60:40, 0.8 ml/min) $R_t$=22.35 min, diastereomeric purity=98% (de=96%) DC: Si-60, toluene/acetone 9:1, Rf=0.38 ESI-MS: $M^{+1}$=679 [α]D 36.9° (c=1 in ethanol)

2.3 Ethyl (S)-3-[(R)-2-(2-carboxyethyl)-3-oxo-3,4-dihydro-2H-benzo-[1,4]oxazin-6-yl]-2-(2,2-dimethylpropoxycarbonylamino)propionate 9

Hydrogen is passed through a solution of 23 g of 8 (crude product from 2.2) in 230 ml of acetic acid at 60° in the presence of 7.5 g of palladium (10% on activated carbon) for 6 hours. Removal of the catalyst and conventional work-up and recrystallisation from ethanol gives 9.

Yield: 10 g (87%) HPLC (Chromolith™ Performance RP-18e, eluent gradient system: water+0.1% of TFA/acetonitrile+0.1% of TFA 99:1→1:99 in 10 min, 3 ml/min) $R_t$=4.88 min. DC: Si-60, dichloromethane/methanol 9:1, Rf=0.42 ESI-MS: $M^{+1}$=451 [α]$_D$=+9.60 (c=1 in methanol) m.p. 99-102°.

2.4 Ethyl 2-(S)-(2,2-di methylpropoxycarbonylamino)-3-{3-oxo-2-(R)-[2-(1H-imidazol-2-ylcarbamoyl)ethyl]-3,4-dihydro-2H-benzo[1,4]oxazin-6-yl}-propionate 10

4.6 g of potassium carbonate are added to a solution of 10 g of 9, 4.4 g of 2-aminoimidazole sulfate, 9.26 g of TBTU and 0.9 g of HOBt in 100 ml of absolute DMF, and the mixture is stirred at 70° under nitrogen for 16 hours. The mixture is cooled to room temperature, poured into 750 ml of cold water, the precipitate is separated off, washed with cold water and dried. The crude product is treated with hot acetonitrile and filtered off after cooling. The residue is recrystallised from ethanol, giving 10.

Yield: 8.5 g (74%) HPLC (Chromolith™ Performance RP-18e, eluent gradient system: water+0.1% of TFA/acetonitrile+0.1% of TFA 99:1→1:99 in 10 min, 3 ml/min) $R_t$=4.48 min. Chiral HPLC: (Chiralpak™ AD, 250 mm, heptane/ethanol 40:60, 0.8 ml/min) $R_t$=21.95 min, diastereomeric purity=99% (de=98%) DC: Si-60, dichloromethane/methanol 9:1, Rf=0.35 ESI-MS: $M^{+1}$=516 m.p. 210° C. (decomposition)

2.5 (S)-2-(2,2-Dimethylpropoxycarbonylamino)-3-{(R)-2-[2-(1H-imidazol-2-ylcarbamoyl)ethyl]-3-oxo-3,4-dihydro-2H-benzo[1,4]oxazin-6-yl}-propionic acid, sodium salt 11

13.6 ml of 2N NaOH are added to a solution of 7 g of 10 in 70 ml of dioxane, and the mixture is stirred at room temperature for a further 16 hours. The mixture is neutralised using dilute HCl, the dioxane is removed under reduced pressure, diluted with water, acidified, and the precipitate is separated off and washed with water. Drying gives 11 as free acid.

Yield: 5.1 g (77%).

For the preparation of the sodium salt, the product is dissolved in one equivalent (10.46 ml) of 1 N NaOH and subsequently lyophilised.

Yield: 5.3 g HPLC (Chromolith™ Performance RP-18e, eluent gradient system: water+0.1% of TFA/acetonitrile+0.1% of TFA 99:1→1:99 in 10 min, 3 ml/min) $R_t$=3.79 min. Resolution of the diastereomers: LiChroSorb™ RP-18, 250/4 mm, eluent: 0.05 M (NH$_4$)H$_2$PO$_4$ buffer pH 4.0/acetonitrile 82/18, 0.8 ml/min, $R_t$=36.7 min ESI-MS: $M^{+1}$=488 [α]$_D$=+18° (c=1 in DMSO) m.p. 185° (decomposition).

EXAMPLE 3

The preparation of (S)-2-(2,2-dimethylpropoxycarbonylamino)-3-{(S)-2-[2-(1H-imidazol-2-ylcarbamoyl)ethyl]-3-oxo-3,4-dihydro-2H-benzo[1,4]oxazin-6-yl}propionic acid (16) is carried out analogously to the following scheme via Mitunobu reaction:

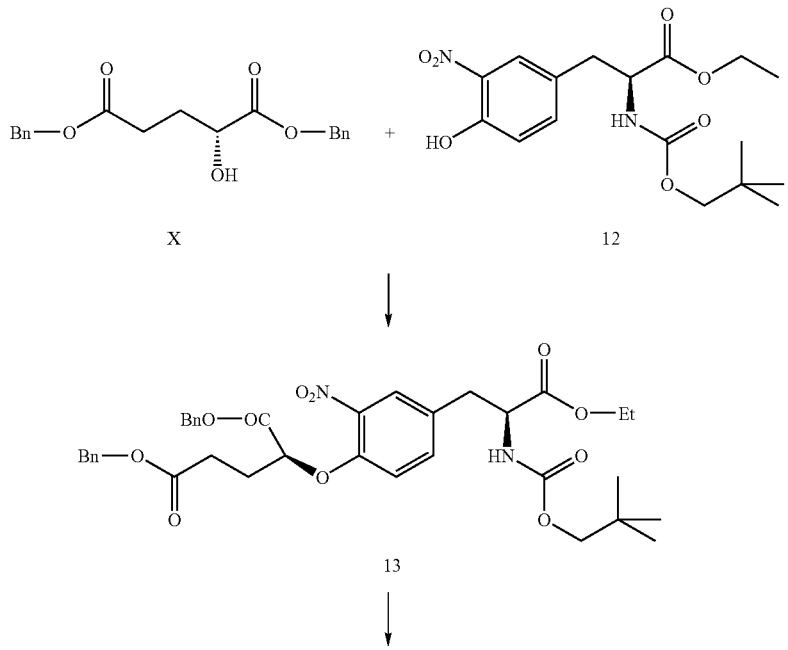

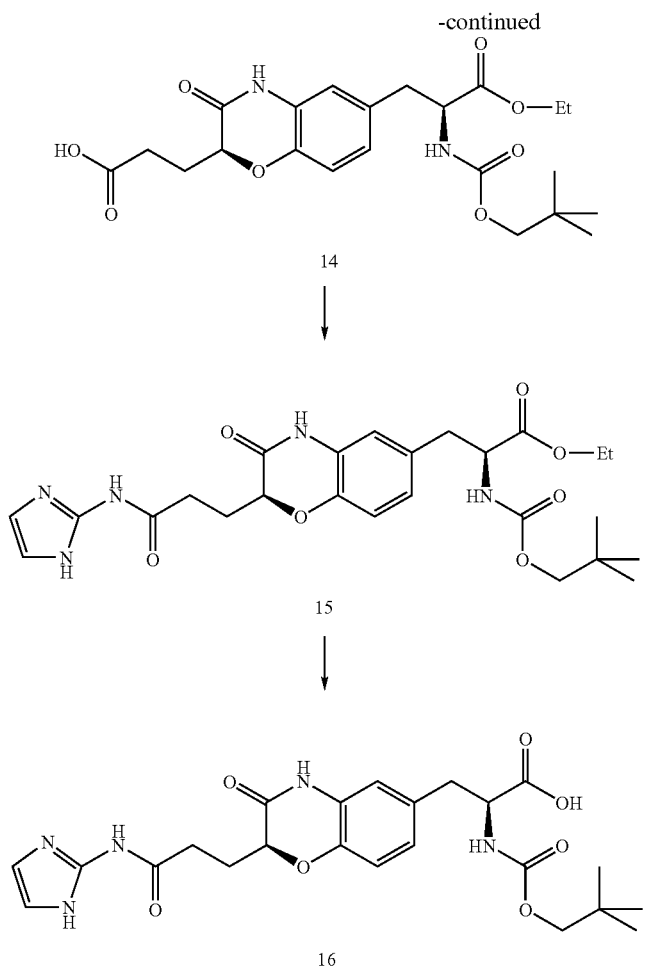

3.1 Ethyl (S)-2-(2,2-dimethylpropoxycarbonylamino)-3-(4-hydroxy-3-nitrophenyl)propionate 12

81.3 g of NaHCO$_3$ are added in small portions to a solution of 206.4 g of (S)-3-nitrotyrosine ethyl ester tosylate in 750 of water and 250 ml of THF. A solution of 60 ml of 2,2-dimethylpropyl chloroformate (neopentyl chloroformate) in 250 ml of THF is then slowly added dropwise, and the mixture is stirred at room temperature for a further 2 hours. After removal of the solvent, the mixture is subjected to conventional work-up, giving 12.

Yield: 107 g (72%) HPLC (Chromolith™ Performance RP-18e, eluent gradient system: water+0.1% of TFA/acetonitrile+0.1% of TFA 99:1→1:99 in 10 min, 3 ml/min) R$_t$=5.68 min. DC: Si-60, toluene/acetone 9:1, Rf=0.42 ESI-MS: M$^{+1}$=369 m.p. 64-67°

[α]$_D$=+0.9° (c=1 in methanol).

3.2 Dibenzyl (R)-2-{4-[(S)-2-(2,2-dimethylpropoxycarbonylamino)-2-ethoxycarbonylethyl]-2-nitrophenoxy}pentanedicarboxylate 13

5.43 g of polymer-bound DEAD (diethyl azodicarboxylate) in 30 ml of THF are added to a solution of 4 g of 12 and 5.35 g of dibenzyl 2-hydroxypentanedicarboxylate (X) in anhydrous THF. The mixture is shaken for 16 hours. The polymer is separated off, and the solvent is removed. The residue is taken up in ethyl acetate, and conventional work-up gives 13, which is not purified further for the further reaction.

Yield: 8.9 g (80% purity), colourless syrup; HPLC (Chromolith™ Performance RP-18e, eluent gradient system: water+0.1% of TFA/acetonitrile+0.1% of TFA 99:1→1:99 in 10 min, 3 ml/min) R$_t$=7.23 min. Chiral HPLC: (Chiralpak™ AD, 250 mm, heptane/isopropanol 60:40, 0.8 ml/min) R$_t$=19.25 min, diastereomeric purity=99% DC: Si-60, toluene/acetone 9:1, Rf=0.38 ESI-MS: M$^{+1}$=679.

3.3 Ethyl (2S)-3-[(2S)-2-(2-carboxyethyl)-3-oxo-3, 4-d i hydro-2H-benzo-[1,4]oxazin-6-yl]-2-(2,2-dimethylpropoxycarbonylamino)propionate 14

Hydrogen is passed through a solution of 8.4 g of 13 (crude product from 3.3) in 80 ml of acetic acid at 60° in the presence of 2.5 g of palladium (10% on activated carbon) for 5 hours. After removal of the catalyst, 15 g of zinc powder are added, and the mixture is stirred at 60° for a further one 1 hour. The mixture is filtered through silica gel, the solvent is removed, the residue is taken up in ethyl acetate, the solution is subjected to conventional work-up, giving amorphous 14.

Yield: 3.8 g (85%) HPLC (Chromolith™ Performance RP-18e, eluent gradient system: water+0.1% of TFA/acetonitrile+0.1% of TFA 99:1→1:99 in 10 min, 3 ml/min) $R_t$=4.83 min. DC: Si-60, dichloromethane/methanol 9:1, Rf=0.42 ESI-MS: $M^{+1}$=451

3.4 Ethyl 2-(S)-(2,2-dimethylpropoxycarbonylamino)-3-{3-oxo-2-(S)-[2-(1H-imidazol-2-ylcarbamoyl)ethyl]-3,4-dihydro-2H-benzo[1,4]oxazin-6-yl}-propionate 15

3.2 g of 14 are reacted with 1.88 g of 2-aminoimidazole, 2.96 g of TBTU, 0.29 g of HOBt and 2.95 g of potassium carbonate in 40 ml of DMF analogously to the preparation of 5. Conventional work-up gives 15.

Yield: 2.4 g (66%)

HPLC (Chromolith™ Performance RP-18e, eluent gradient system: water+0.1% of TFA/acetonitrile+0.1% of TFA 99:1→1:99 in 10 min, 3 ml/min) $R_t$=4.40 min.

Chiral HPLC: (Chiralpak™ AD, 250 mm, heptane/ethanol 40:60, 0.8 ml/min) $R_t$=28.0 min, diastereomeric purity=99%

DC: Si-60, dichloromethane/methanol 9:1, Rf=0.33
ESI-MS: $M^{+1}$=516.

3.5 (S)-2-(2,2-Dimethylpropoxycarbonylamino)-3-{(S)-2-[2-(1H-imidazol-2-ylcarbamoyl)ethyl]-3-oxo-3,4-dihydro-2H-benzo[1,4]oxazin-6-yl}-propionic acid 16

The ester cleavage of 2 g of 15 is carried out analogously to the preparation of 10.

Yield: 1.7 g (90%) HPLC (Chromolith™ Performance RP-18e, eluent gradient system: water+0.1% of TFA/acetonitrile+0.1% of TFA 99:1→1:99 in 10-min, 3 ml/min) $R_t$=3.68 min.

Resolution of the diastereomers: LiChroSorb™ RP-18, 250/4 mm, eluent: 0.05 M $(NH_4)H_2PO_4$ buffer pH 4.0/acetonitrile 82/18, 0.8 ml/min, $R_t$=33.07 min
ESI-MS: $M^{+1}$=488.

EXAMPLE 4 (COMPARATIVE EXPERIMENT)

The preparation of tert-butyl 2-(S)-(2,2-dimethylpropoxycarbonylamino)-3-[2-(2-carboxyethyl)-3-oxo-3,4-dihydro-2H-benzo[1,4]oxazin-6-yl]propionate 20 analogously to WO 98/35949 (Example 11):

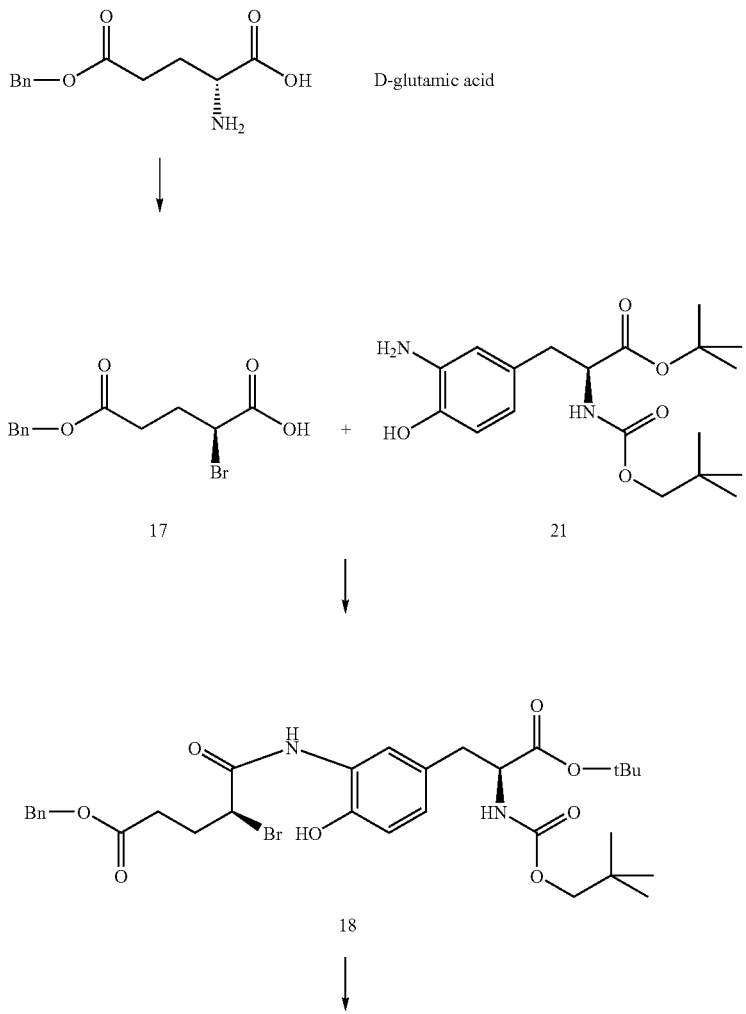

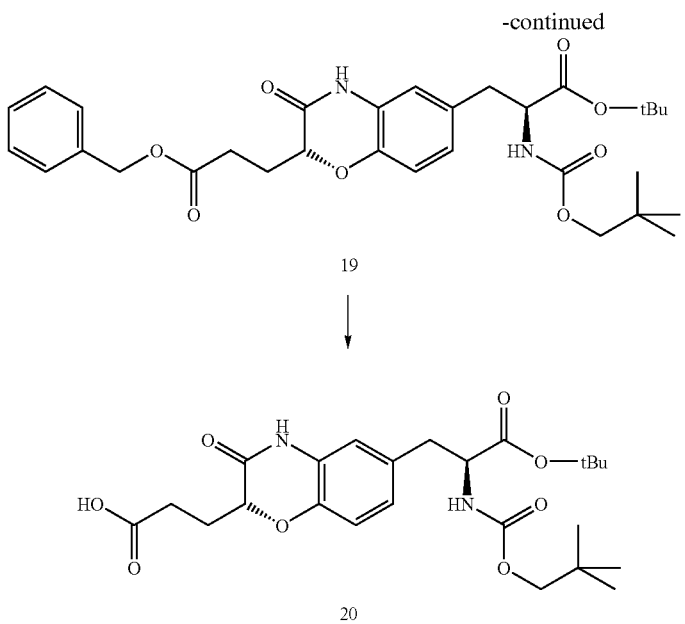

4.1 5-Benzyl 2-bromopentanedicarboxylate 17

50 g of sodium nitrite are added in portions at 0-5° to a solution of 115 g of 5-benzyl D-glutamate and 190 g of KBr in 1.4 l of 2.5N sulfuric acid, and the mixture is stirred for a further 1 hour, later at room temperature for a further 1 hour. Conventional work-up gives 17.

Yield: 101.6 g (70%)
HPLC (Chromolith™ Performance RP-18e, eluent gradient system: water+0.1% of TFA/acetonitrile+0.1% of TFA 99:1→1:99 in 10 min, 3 ml/min) $R_t$=4.91 min.
ESI-MS: $M^{+1}$=302.

4.2 Benzyl (S)-4-bromo-4-{5-[(S)-2-(2,2-dimethyl-propoxycarbonylamino)-2-tert-butyloxycarbonyl-ethyl]-2-hydroxyphenylcarbamoyl}butyrate 18

66.3 g of EDCl hydrochloride are added in portions to a solution of 106 g of tert-butyl (S)-2-(2,2-dimethylpropoxy-carbonylamino)-2-(3-amino-4-hydroxyphenyl)propionate (12, obtainable from the corresponding 3-nitro derivative by reduction using $H_2$/Pd, C) and 101 g of 17 in 1 l of absolute THF, and the mixture is stirred for a further 16 hours. The THF is removed, the residue is taken up in ethyl acetate, and the solution is subjected to conventional work-up, giving 18 as yellow syrup, which is used for the further reaction without further purification.

Yield: 216 g (85% purity, 98%)
HPLC (Chromolith™ Performance RP-18e, eluent gradient system: water+0.1% of TFA/acetonitrile+0.1% of TFA 99:1→1:99 in 10 min, 3 ml/min) $R_t$=7.07 min.
DC: Si-60, toluene/acetone 4:1, Rf=0.41
ESI-MS: $M^{+1}$=650.

4.3 tert-Butyl (S)-3-[2-(2-benzyloxycarbonylethyl)-3-oxo-3,4-dihydro-2H-benzo[1,4]oxazin-6-yl]-2-(2,2-dimethylpropoxycarbonylamino)propionate 19

43.14 of DBU are added to a solution of 215 g of 18 in 1250 ml of toluene, and the mixture is stirred at room temperature for a further one hour. The solvent is removed, and the residue is purified by flash chromatography over silica gel (eluent toluene/acetone gradient 20:1→4:1).

Chiral HPLC shows a diastereomeric ratio of 2:1 of the R/S and S/S configured benzoxazinone derivatives.

Yield: 69 g (43%)
HPLC (Chromolith™ Performance RP-18e, eluent gradient system: water+0.1% of TFA/acetonitrile+0.1% of TFA 99:1→1:99 in 10 min, 3 ml/min) $R_t$=7.01 min.
Chiral HPLC: (Chiralpak™ AD, 250 mm, ethanol, 0.8 ml/min) $R_t$=12.88 min, diastereomeric purity=61% (de=22%)
DC: Si-60, toluene/acetone 4:1, Rf=0.27
ESI-MS: $M^{+1}$=569.

4.4 tert-Butyl 2-(S)-(2,2-dimethylpropoxycarbonylamino)-3-[2-(2-carboxyethyl)-3-oxo-3,4-dihydro-2H-benzo[1,4]oxazin-6-yl]propionate 20

Hydrogen is passed through a solution of 26 g of 13 in 250 ml of THF at room temperature in the presence of 6.5 g of palladium (10% on activated carbon) for 6 hours. The catalyst is separated off, the solvent is removed, and the residue is dried under reduced pressure.

Yield: 21.5 g (98%) of amorphous foam
HPLC (Chromolith™ Performance RP-18e, eluent gradient system: water+0.1% of TFA/acetonitrile+0.1% of TFA 99:1→1:99 in 10 min, 3 ml/min) $R_t$=5.63 min.
DC: Si-60, dichloromethane/methanol 9:1, Rf=0.44
ESI-MS: $M^{+1}$=479.

EXAMPLE 5

The amine derivatisation of the benzoxazinone is carried out analogously to the following scheme:

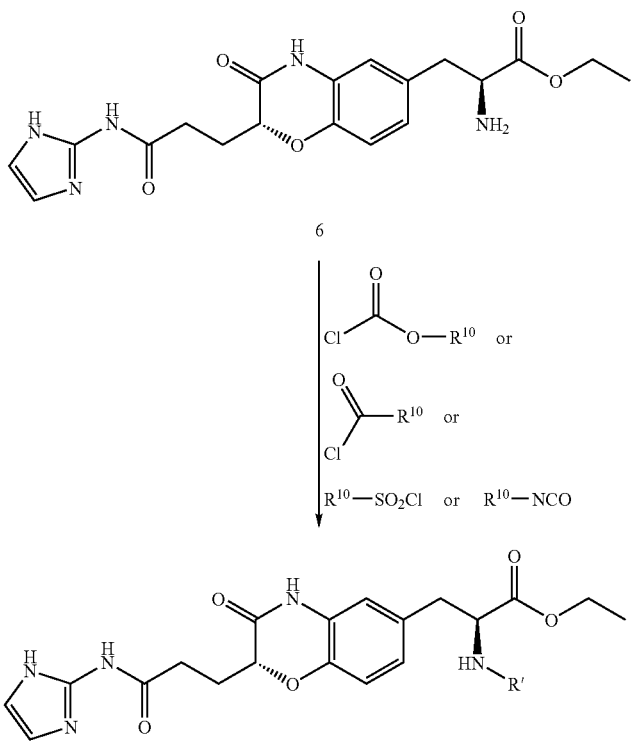

R¹⁰ has the meanings as indicated in claim 1.

5.1 Sulfonylation:

A solution of the amine 6 in absolute DMF is reacted at room temperature with 1.1 equivalents of an alkyl- or arylsulfonyl chloride and 3 equivalents of triethylamine. After the reaction, the mixture is subjected to conventional work-up.

Thus, reaction of
ethyl 2-(S)-amino-3-{3-oxo-2-(R)-[2-(1H-imidazol-2-ylcarbamoyl)ethyl]-3,4-dihydro-2H-benzo[1,4]oxazin-6-yl}propionate with
 butylsulfonyl chloride,
 4-tolylsulfonyl chloride,
 benzylsulfonyl chloride,
 (R or S)-camphor-10-sulfonyl chloride gives the following compounds
ethyl 2-(S)-butylsulfonamido-3-{3-oxo-2-(R)-[2-(1H-imidazol-2-ylcarbamoyl)ethyl]-3,4-dihydro-2H-benzo[1,4]oxazin-6-yl}propionate,
ethyl 2-(S)-(4-tolylsulfonamido)-3-{3-oxo-2-(R)-[2-(1H-imidazol-2-ylcarbamoyl)ethyl]-3,4-dihydro-2H-benzo[1,4]oxazin-6-yl}propionate,
ethyl 2-(S)-benzylsulfonamido-3-{3-oxo-2-(R)-[2-(1H-imidazol-2-ylcarbamoyl)ethyl]-3,4-dihydro-2H-benzo[1,4]oxazin-6-yl}propionate,
ethyl 2-(S)-[(R)-camphor-10-ylsulfonamido]-3-{3-oxo-2-(R)-[2-(1H-imidazol-2-ylcarbamoyl)ethyl]-3,4-dihydro-2H-benzo[1,4]oxazin-6-yl}-propionate,
ethyl 2-(S)-[(S)-camphor-10-ylsulfonamido]-3-{3-oxo-2-(R)-[2-(1H-imidazol-2-ylcarbamoyl)ethyl]-3,4-dihydro-2H-benzo[1,4]oxazin-6-yl}-propionate.

5.2 Carbamate Formation

A solution of the amine 5 in absolute DMF is reacted at room temperature with 1.1 equivalents of an alkyl or aryl chloroformate or with an alkyl or aryl dicarbonate and 3 equivalents of triethylamine. After the reaction, the mixture is subjected to conventional work-up.

Thus, reaction of
ethyl 2-(S)-amino-3-{3-oxo-2-(R)-[2-(1H-imidazol-2-ylcarbamoyl)ethyl]-3,4-dihydro-2H-benzo[1,4]oxazin-6-yl}propionate with
 isopropyl chloroformate,
 benzyl chloroformate gives the following compounds
ethyl 2-(S)-isobutoxycarboxamido-3-{3-oxo-2-(R)-[2-(1H-imidazol-2-ylcarbamoyl)ethyl]-3,4-dihydro-2H-benzo[1,4]oxazin-6-yl}propionate,
ethyl 2-(S)-benzyloxycarboxamido-3-{3-oxo-2-(R)-[2-(1H-imidazol-2-ylcarbamoyl)ethyl]-3,4-dihydro-2H-benzo[1,4]oxazin-6-yl}propionate.

5.3 Acylation

A solution of the amine 5 in absolute DMF is reacted at room temperature with 1.1 equivalents of an alkyl- or arylcarbonyl chloride and 3 equivalents of triethylamine. After the reaction, the mixture is subjected to conventional work-up.

Alternatively, a very wide variety of variants can be employed, such as, for example, with EDCl, activated esters, HOBt/TBTU.

5.4 Urea Formation

A solution of the amine 5 in absolute DMF is reacted at room temperature with 1.1 equivalents of an alkyl or aryl isocyanate and 3 equivalents of triethylamine. After the reaction, the mixture is subjected to conventional work-up.

The invention claimed is:

1. A process for preparing a compound of formula I

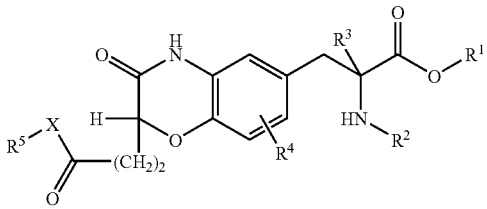

in which
- $R^1$ denotes H, alkyl having 1, 2, 3, 4, 5 or 6 C atoms or benzyl,
- $R^2$ denotes $R^{10}$, CO—$R^{10}$, COOR$^6$, COOR$^{10}$, CONHR$^{10}$, SO$_2$R$^6$ or SO$_2$R$^{10}$,
- $R^3$ denotes H or alkyl having 1-6 C atoms,
- $R^4$ denotes H, Hal, OA, NHR$^{10}$, N(R$^{10}$), —NH-acyl, —O-acyl, CN, NO$_2$, OR$^{10}$, SR$^{10}$, R$^2$ or CONHR$^{10}$,
- $R^5$ denotes NH$_2$, H$_2$N—C(=NH) or H$_2$N-(C=NH)—NH, in which the primary amino group is optionally provided with an amino-protecting group, and is optionally mono-, di- or trisubstituted by R$^{10}$, CO—R$^{10}$, COOR$^{10}$ or SO$_2$R$^{10}$, or denotes R$^6$,
- X is absent or denotes NH,
- $R^6$ denotes a mono- or bicyclic saturated, unsaturated or aromatic heterocycle having 1 to 4 N, O and/or S atoms, which is optionally unsubstituted or mono-, di- or trisubstituted by Hal, A, —CO -A, OA, CN, COOH, COOA, CONHA, NO$_2$, =NH or =O,
- $R^9$ denotes H, Hal, OA, NHA, NAA', NHacyl, Oacyl, CN, NO$_2$, SA, SOA, SO$_2$A, SO$_2$Ph or SO$_3$H,
- $R^{10}$ denotes H, A, Ar or aralkylene having 7-14 C atoms,
- A, A' each, independently of one another, denote H or alkyl having 1-15 C atoms or cycloalkyl having 3-15 C atoms, each of which is unsubstituted or mono-, di- or trisubstituted by R$^9$, and in which one, two or three methylene groups are optionally replaced by —NH—, O and/or S,
- Ar denotes mono- or bicyclic aromatic ring system having 0, 1, 2, 3 or 4 N, O and/or S atoms which is unsubstituted or mono-, di- or trisubstituted by A and/or R$^9$,
- Ph denotes phenyl which is unsubstituted or mono-, di- or trisubstituted by A,
- Hal denotes F, Cl, Br or I, or a pharmaceutically acceptable salt or solvate, thereof, comprising a) reacting 5-oxotetrahydrofuran-2-carboxylic acid with a compound of the formula II

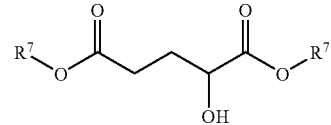

in which
- $R^7$ denotes benzyl or alkyl having 1, 2, 3, 4, 5 or 6 C atoms, and
- L denotes Cl, Br, I or a free or reactively functionally modified OH group, to give a compound of the formula III

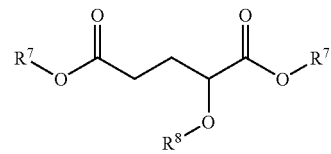

in which
- $R^7$ denotes benzyl or alkyl having 1, 2, 3, 4, 5 or 6 C atoms, b) then reacting a compound of the formula III with a compound of the formula IV $$R^8\text{-L} \qquad \qquad IV$$

in which
- $R^8$ denotes alkylsulfonyl having 1-6 C atoms or arylsulfonyl having 6-10 C atoms, and
- L denotes Cl, Br, I or a free or reactively functionally modified OH group, to give a compound of the formula V

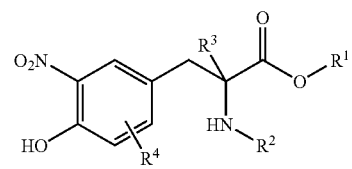

in which
- $R^7$ denotes benzyl or alkyl having 1, 2, 3, 4, 5 or 6 C atoms, and
- $R^8$ denotes alkylsulfonyl having 1-6 C atoms or arylsulfonyl having 6-10 C atoms, c) then reacting a compound of formula III or V with a compound of formula VI in which
- $R^1$ denotes H, alkyl having 1, 2, 3, 4, 5 or 6 C atoms or benzyl,
- $R^2$ denotes $R^{10}$, CO—$R^{10}$, COOR$^6$, COOR$^{10}$, CONHR$^{10}$, SO$_2$R$^6$ or SO$_2$R$^{10}$,
- $R^3$ denotes H or alkyl having 1-6 C atoms,
- $R^4$ denotes H, Hal, OA, NHR$^{10}$, N(R$^{10}$)$_2$, —NH-acyl, —O-acyl, CN, NO$_2$, OR$^{10}$, SR$^{10}$, R$^2$ or CONHR$^{10}$,
- $R^6$ denotes a mono- or bicyclic saturated, unsaturated or aromatic heterocycle having 1 to 4 N, O and/or S atoms, which is unsubstituted or mono-, di- or trisubstituted by Hal, A, —CO-A, OA, CN, COOH, COOA, CONHA, NO$_2$, =NH or =O,
- $R^9$ denotes H, Hal, OA, NHA, NAA', NHacyl, Oacyl, CN, NO$_2$, SA, SOA, SO$^2$A, SO$_2$ Ph or SO$_3$H, $R^{10}$ denotes H, A, Ar or aralkylene having 7-14 C atoms, A, A' each, independently of one another, denote H or alkyl having 1-15 C atoms or cycloalkyl having 3-15 atoms, each of which is unsubstituted or mono-, di- or trisubstituted by $R^9$, and in which one, two or three methylene groups are optionally replaced by —NH—, O and/or S, Ar denotes mono- or bicyclic aromatic ring system having 0, 1, 2, 3 or 4 N, O and/or S atoms which is unsubstituted or mono-, di- or trisubstituted by A and/or $R^9$, Ph denotes phenyl which is unsubstituted or mono-, di- or trisubstituted by A, Hal denotes F, Cl, Br or I, to give a compound of formula VII

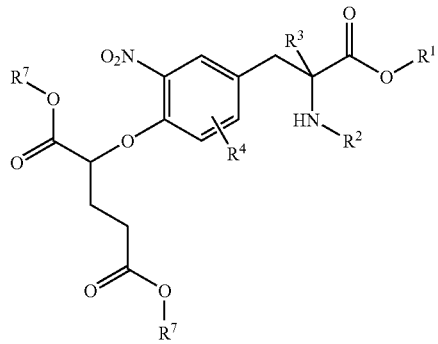

VII in which $R^1$ denotes H, alkyl having 1, 2, 3, 4, 5 or 6 C atoms or benzyl, $R^2$ denotes $R^{10}$, CO—$R^{10}$, COOR$^6$, COOR$^{10}$, CONHR$^{10}$, SO$_2$R$^6$ or SO$_2$R$^{10}$, $R^3$ denotes H or alkyl having 1-6 C atoms, $R^4$ denotes H, Hal, OA, NHR$^{10}$, N(R$^{10}$)$_2$, —NH-acyl, —O-acyl, CN, NO$_2$, OR$^{10}$, SR$^{10}$, or CONHR$^{10}$, $R^6$ denotes a mono- or bicyclic saturated, unsaturated or aromatic heterocycle having 1 to 4 N, O and/or S atoms, which is unsubstituted or mono-, di- or trisubstituted by Hal, A, —CO-A, OA, CN, COOH, COOA, CONHA, NO$_2$, =NH or =O, $R^7$ denotes benzyl or alkyl having 1, 2, 3, 4, 5 or 6 C atoms, $R^9$ denotes H, Hal, OA, NHA, NAA', NHacyl, Oacyl, CN, NO$_2$, SA, SOA, SO$_2$A, SO$_2$Ph or SO$_3$H, $R^{10}$ denotes H, A, Ar or aralkylene having 7-14 C atoms, A, A' each, independently of one another, denote H or alkyl having 1-15 C atoms or cycloalkyl having 3-15 C atoms, each of which is unsubstituted or mono-, di- or trisubstituted by $R^9$, and in which one, two or three methylene groups are optionally replaced by —NH—, O and/or S, Ar denotes mono- or bicyclic aromatic ring system having 0, 1, 2, 3 or 4 N, O and/or S atoms which is unsubstituted or mono-, di- or trisubstituted by A and/or $R^9$, Ph denotes phenyl which is unsubstituted or mono-, di- or trisubstituted by A, Hal denotes F, Cl, Br or I, d) then converting a compound of formula VII into a compound of formula VIII

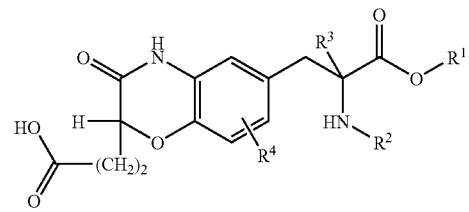

VIII in which $R^1$ denotes H, alkyl having 1, 2, 3, 4, 5 or 6 C atoms or benzyl, $R^2$ denotes $R^{10}$, CO—$R^{10}$, COOR$^6$, COOR$^{10}$, CONHR$^{10}$, SO$_2$R$^6$ or SO$_2$R$^{10}$, $R^3$ denotes H or alkyl having 1-6 C atoms, $R^4$ denotes H, Hal, OA, NHR$^{10}$, N(R$^{10}$)$_2$, —NH-acyl, —O-acyl, CN, NO$_2$, OR$^{10}$, SR$^{10}$, $R^2$ or CONHR$^{10}$, $R^6$ denotes a mono- or bicyclic saturated, unsaturated or aromatic heterocycle having 1 to 4 N, O and/or S atoms, which is unsubstituted or mono-, di- or trisubstituted by Hal, A, —CO-A, OA, CN, COOH, COOA, CONHA, NO$_2$, =NH or =O, $R^9$ denotes H, Hal, OA, NHA, NAA', NHacyl, Oacyl, CN, NO$_2$, SA, SOA, SO$_2$A, SO$_2$Ph or SO$_3$H, $R^{10}$ denotes H, A, Ar or aralkylene having 7-14 C atoms, A, A' each, independently of one another, denote H or alkyl having 1-15 C atoms or cycloalkyl having 3-15 C atoms, each of which is unsubstituted or mono-, di- or trisubstituted by $R^9$, and in which one, two or three methylene groups are optionally replaced by —NH—, O and/or S, Ar denotes mono- or bicyclic aromatic ring system having 0, 1, 2, 3 or 4 N, O and/or S atoms which is unsubstituted or mono-, di- or trisubstituted by A and/or $R^9$, Ph denotes phenyl which is unsubstituted or mono-, di- or trisubstituted by A, Hal denotes F, Cl, Br or I, e) subsequently, optionally, a compound of the formula VIII is converted into a compound of formula VIIIa

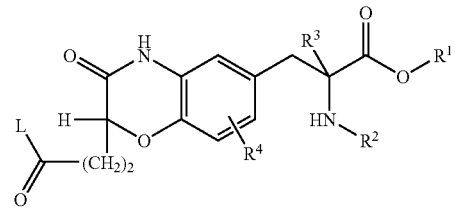

VIIIa in which $R^1$, $R^2$, $R^3$ and $R^4$ have the meanings indicated under d), and L denotes Cl, Br, I or a reactively functionally modified OH group, e) then reacting a compound of the formula VIII or a compound of formula VIIIa e) i) with a compound of formula IX $$R^5—H \qquad IX$$

in which $R^5$ denotes NH$_2$, H$_2$N—C(=NH) or H$_2$N—(C=NH)—NH, in which the primary amino group is optionally provided with an amino-protecting group, and is optionally mono-, di- or trisubstituted by $R^{10}$, CO—$R^{10}$, COOR$^{10}$ or SO$_2$R$^{10}$, in which $R^{10}$ has the meanings indicated for formula I, or e) ii) with a compound of formula X $$R^6\text{—}NH_2 \qquad \qquad X$$

in which $R^6$ denotes a mono- or bicyclic saturated, unsaturated or aromatic heterocycle having 1 to 4 N, O and/or S atoms, which is unsubstituted or mono-, di- or trisubstituted by Hal, A, —CO-A, OA, CN, COOH, COOA, CONHA, NO$_2$, =NH or =O, to give a compound of formula I, subsequently, optionally, converting a radical $R^2$ into another radical $R^2$ by reacting a compound of formula I in which $R^2$ denotes H with L-R$^{10}$, L-CO—R$^{10}$, L-COOR$^6$, L-COOR$^{10}$, R$^{10}$—N=C=O, R$^6$—SO$_2$L, or R$^{10}$—SO$_2$L, in which $R^{10}$ denotes A, Ar or aralkylene having 7-14 C atoms, and L denotes Cl, Br, I or a free or reactively functionally modified OH group, and optionally converting a base or acid of a compound of formula I into one of its pharmaceutically acceptable salts.

2. A process according to claim 1, in which
$R^3$ denotes H, and
$R^4$ denotes H.

3. A process according to claim 1, in which
$R^6$ denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl.

4. A process according to claim 1, in which
$R^9$ denotes H.

5. A process according to claim 1, in which
$R^{10}$ denotes H, alkyl having 1, 2, 3, 4, 5 or 6 C atoms, camphor-10-yl or benzyl.

6. A process according to claim 1, in which
A denotes unsubstituted alkyl having 1-15 C atoms or cycloalkyl having 3-15 C atoms.

7. A process according to claim 1, in which
A denotes alkyl having 1, 2, 3, 4, 5 or 6 C atoms, and
$^{10}$ denotes H, alkyl having 1, 2, 3, 4, 5 or 6 C atoms, camphor-10-yl or benzyl.

8. A process according to claim 1, in which
$R^1$ denotes H, alkyl having 1, 2, 3, 4, 5 or 6 C atoms or benzyl,
$R^2$ denotes $R^{10}$, CO—R$^{10}$, COOR$^{10}$ or SO$_2$R$^{10}$,
$R^3$ denotes H,
$R^4$ denotes H,
$R^5$ denotes $R^6$,
$R^6$ denotes a mono- or bicyclic saturated, unsaturated or aromatic heterocycle having 1 to 4 N, O and/or S atoms, which is unsubstituted or mono-, di- or trisubstituted by Hal, A, —CO-A, OA, CN, COOH, COOA, CONHA, NO$_2$, =NH or =O,
X denotes NH,
$R^{10}$ denotes H, alkyl having 1, 2, 3, 4, 5 or 6 C atoms, camphor-10-yl or benzyl,
A denotes alkyl having 1, 2, 3, 4, 5 or 6 C atoms, and
Hal denotes F, Cl, Br or I.

9. A process according to claim 8, in which
$R^6$ denotes 1H-imidazoi-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl.

10. A process for preparing a compound of formula Ia

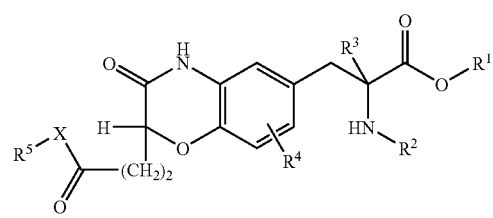

in which
$R^1$ denotes H or alkyl having 1, 2, 3 or 4 C atoms,
$R^2$ denotes $R^{10}$, CO—R$^{10}$, COOR$^{10}$ or SO$_2$R$^{10}$,
$R^3$ denotes H,
$R^4$ denotes H,
$R^5$ denotes $R^6$,
X denotes NH,
$R^6$ denotes 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-A-1,5-dihydroimidazol-4-on-2-yl, pyrimidin-2-yl or 1,4,5,6-tetrahydropyrimidin-2-yl,
$R^{10}$ denotes H or alkyl having 1, 2, 3, 4, 5 or 6 C atoms, and
A denotes alkyl having 1, 2, 3, 4, 5 or 6 C atoms, or a pharmaceutically acceptable salt or solvate thereof, where comprising a) reacting 5-oxotetrahydrofuran-2-carboxylic acid with a compound of formula II $$R^7\text{-L} \qquad \qquad II$$

in which
$R^7$ denotes benzyl or alkyl having 1, 2, 3, 4, 5 or 6 C atoms, and
L denotes Cl, Br, I or a free or reactively functionally modified OH group, to give a compound of formula III

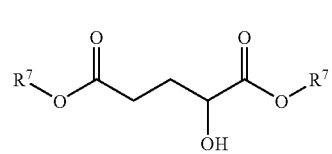

in which
$R^7$ denotes benzyl or alkyl having 1, 2, 3, 4, 5 or 6 C atoms, b) then reacting a compound of formula III with a compound of formula IV $$R^8\text{-L} \qquad \qquad IV$$

in which
$R^8$ denotes alkylsulfonyl having 1-6 C atoms or arylsulfonyl having 6-10 C atoms, and
L denotes Cl, Br, I or a free or reactively functionally modified OH group, to give a compound of formula V

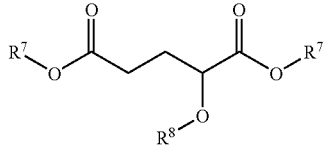

in which
- $R^7$ denotes benzyl or alkyl having 1, 2, 3, 4, 5 or 6 C atoms, and
- $R^8$ denotes alkylsulfonyl having 1-6 C atoms or arylsulfonyl having 6-10 C atoms,
- c) then reacting a compound of the formula III or V with a compound of formula VI

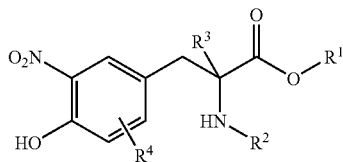

in which
- $R^1$ denotes H or alkyl having 1, 2, 3 or 4 C atoms,
- $R^2$ denotes $R^{10}$, CO—$R^{10}$, COO$R^{10}$ or SO$_2R^{10}$,
- $R^3$ denotes H,
- $R^4$ denotes H,
- $R^{10}$ denotes H or alkyl having 1, 2, 3, 4, 5 or 6 C atoms, to give a compound of the formula VII

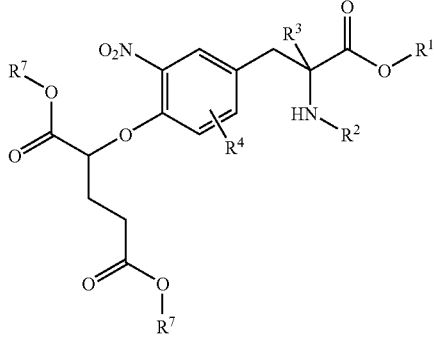

in which
- $R^1$ denotes H or alkyl having 1, 2, 3 or 4 C atoms,
- $R^2$ denotes $R^{10}$, CO—$R^{10}$, COO$R^{10}$ or SO$_2R^{10}$,
- $R^3$ denotes H,
- $R^4$ denotes H,
- $R^7$ denotes benzyl or alkyl having 1, 2, 3, 4, 5 or 6 C atoms,
- $R^{10}$ denotes H or alkyl having 1, 2, 3, 4, 5 or 6 C atoms,
- d) then converting a compound of formula VII into a compound of formula VIII

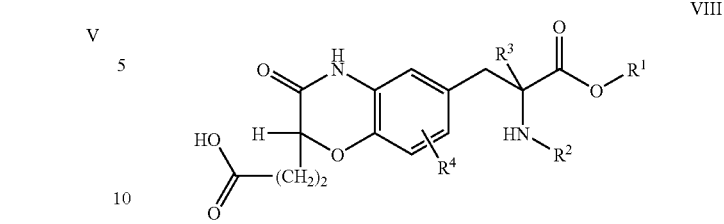

in which
- $R^1$ denotes H or alkyl having 1, 2, 3 or 4 C atoms,
- $R^2$ denotes $R^{10}$, CO—$R^{10}$, COO$R^{10}$ or SO$_2R^{10}$,
- $R^3$ denotes H,
- $R^4$ denotes H,
- $R^{10}$ denotes H or alkyl having 1, 2, 3, 4, 5 or 6 C atoms,
- e) then reacting a compound of formula VIII with a compound of formula X

in which
- $R^6$ denotes 1H-imidazol-2-yl, thiazol-2-yl, 1H-benzimidazol-2-yl, 2H-pyrazol-2-yl, 1H-tetrazol-5-yl, 2-iminoimidazohdin-4-on-5-yl, 1-A-1,5-dihydroimidazol-4-on-2-yl, pyrimidin-2-yl or 1,4,5,6-tetrahydropyrimidin-2-yl, to give a compound of formula Ia, subsequently, optionally, converting a radical $R^2$ into another radical $R^2$ by reacting a compound of the formula Ia in which $R^2$ denotes H with L-$R^{10}$, L-CO—$R^{10}$, L-COO$R^{10}$ or $R^{10}$—SO$_2$L, in which
- $R^7$ denotes alkyl having 1, 2, 3, 4, 5 or 6 C atoms, and
- L denotes Cl, Br, I or a free or reactively functionally modified OH group, and optionally converting a base or acid of formula Ia into one of its pharmaceutically acceptable salts.

11. A process according to claim 1, in which $R^6$ denotes 1H-imidazol-2-yl.

12. A process according to claim 1, in which in step b), in the compounds of formula IV and V, $R^8$ denotes methylsulfonyl, trifluoromethylsulfonyl, phenylsulfonyl or p-tolylsulfonyl.

13. A process according to claim 1, where the conversion of a compound of formula VII into a compound of formula VIII is carried out
- a) by reduction of the nitro group, subsequent ester cleavage and cyclization, or
- b) by ester cleavage, subsequent reduction of the nitro group and cyclization.

14. A process for preparing (S)-2-(2,2-dimethylpropoxycarbonylamino)-3-{(S)-2-[2-(1H-imidazol-2-ylcarbamoyl)ethyl]-3-oxo-3,4-dihydro-2H-benzo [1,4]oxazin-6-yl}propionic acid, comprising
- a) reacting (S)-3-nitrotyrosine ethyl ester tosylate with 2,2-dimethylpropyl chloroformate to give ethyl (S)-2-(2,2-dimethylpropoxy-carbonylamino) -3-(4-hydroxy-3-nitrophenyl)propionate (12),
- b) reacting (12) with dibenzyl 2-hydroxypentanedicarboxylate to give dibenzyl (R)-2-{4-[(S)-2-(2,2-dimethylpropoxycarbonylamino)-2-ethoxy-carbonylethyl]-2-nitrophenoxy}pentanedicarboxylate (13), c) cyclizing (13) to give ethyl (2S)-3-[(2S)-2-(2-carboxy-ethyl)-3-oxo-3,4-dihydro-2H-benzo[1,4]oxazin-6-yl]-2-(2,2-dimethylpropoxycarbonyl-amino) propionate (14), d) reacting (14) with 2-aminoimidazole to give ethyl 2-(S)-(2,2-dimethylpropoxycarbonylamino) -3-{3-oxo-2-(S)-[2-(1H-imidazol-2-yl-carbamoyl) ethyl]-3,4-dihydro-2H-benzo[1,4]oxazin-6-yl}propionate (15), and e) converting (15) by ester cleavage into (S)-2-(2,2-dimethyl-propoxycarbonylamino) -3-{(S)-2-[2-(1H-imidazol-2-ylcarbamoyl)ethyl]-3-oxo -3,4-dihydro-2H-benzo[1,4]oxazin-6-yl }propionic acid (16).

15. A process according to claim 1, wherein an isolated stereoisomer of a compound of formula I is prepared.

16. A process according to claim 10, wherein an isolated stereoisomer of a compound of formula Ia is prepared.

17. A process according to claim 1, wherein a compound of formula I or a pharmaceutically acceptable salt thereof is prepared.

18. A process according to claim 10, wherein a compound of formula Ia or a pharmaceutically acceptable salt thereof is prepared.

19. A process according to claim 10, in which $R^6$ denotes 1H-imidazol-2-yl; and/or in step b), in the compounds of formula IV and V, $R^8$ denotes methylsulfonyl, trifluoromethylsulfonyl, phenylsulfonyl or p-tolylsulfonyl; and/or the conversion of a compound of formula VII into a compound of formula VIII is carried out a) by reduction of the nitro group, subsequent ester cleavage and cyclization, or b) by ester cleavage, subsequent reduction of the nitro group and cyclization.

20. A process according to claim 14, further comprising converting the (S)-2-(2,2-dimethylpropoxycarbonylamino)-3-{(S)-2-[2-(1H-imidazol-2-ylcarbamoyl)ethyl]-3-oxo-3,4-dihydro-2H-benzo[1,4]oxazin-6-yl}propionic acid into one of its pharmaceutically acceptable salts.

21. A process according to claim 1, wherein each

A, A' each, independently of one another, denote H or alkyl having 1-15 C atoms or cycloalkyl having 3-15 C atoms, each of which is unsubstituted or mono-, di- or trisubstituted by $R^9$.

* * * * *

UNITED STATES PATENT AND TRADEMARK OFFICE
CERTIFICATE OF CORRECTION

| | | |
|---|---|---|
| PATENT NO. | : 7,371,854 B2 | Page 1 of 1 |
| APPLICATION NO. | : 10/545168 | |
| DATED | : May 13, 2008 | |
| INVENTOR(S) | : Matthias Wiesner | |

It is certified that error appears in the above-identified patent and that said Letters Patent is hereby corrected as shown below:

Column 41, line 30 reads "$N(R^{10})$" should read --$N(R^{10})_2$--
Column 41, line 62 reads "compound of the formula" should read --compound of formula--
Column 42, line 3 reads "compound of the formula" should read --compound of formula--
Column 42, line 17 reads "compound of the formula" should read --compound of formula--
Column 42, line 25 reads "compound of the formula" should read --compound of formula--
Column 43, line 3 reads "3-15 atoms" should read --3-15 C atoms--
Column 44, line 41 reads "a compound of the formula" should read --a compound of formula--
Column 44, line 60 reads "a compound of the formula" should read --a compound of formula--
Column 45, line 46 reads "$^{10}$ denotes" should read --$R^{10}$ denotes--
Column 46, line 34 reads "where comprising" should read --comprising--
Column 48, line 27 reads "2-iminoimidazohdin" should read --2-iminoimidazolidin--
Column 48, line 36 reads "$R^7$" should read --$R^{10'}$--

Signed and Sealed this

Twenty-sixth Day of August, 2008

JON W. DUDAS
*Director of the United States Patent and Trademark Office*